United States Patent [19]

Ponsford et al.

[11] 4,210,661
[45] Jul. 1, 1980

[54] SYNTHETIC β-LACTAM COMPOUNDS, A PROCESS FOR THEIR PREPARATION AND COMPOSITIONS CONTAINING THEM

[75] Inventors: Roger J. Ponsford, Horsham; Robert Southgate, Warnham; Patricia M. Roberts, Redhill, all of England

[73] Assignee: Beecham Group Limited, England

[21] Appl. No.: 930,225

[22] Filed: Aug. 2, 1978

[30] Foreign Application Priority Data

Aug. 6, 1977 [GB] United Kingdom ............ 33037/77

[51] Int. Cl.² .................. C07D 487/04; A61K 31/40
[52] U.S. Cl. .............................. 424/274; 260/239 A; 260/326.31; 424/114
[58] Field of Search .................. 260/326.31; 424/274

[56] References Cited

U.S. PATENT DOCUMENTS

| | | | |
|---|---|---|---|
| 3,950,357 | 4/1976 | Kahan et al. | 260/326.31 |
| 4,011,216 | 3/1977 | Menard et al. | 424/274 |

*Primary Examiner*—Mary C. Lee
*Attorney, Agent, or Firm*—Jacobs & Jacobs

[57] ABSTRACT

This invention provides synthetic β-lactam antibacterial compounds, a process for their preparation and pharmaceutical compositions containing them.

The compounds are those of the formula (II):

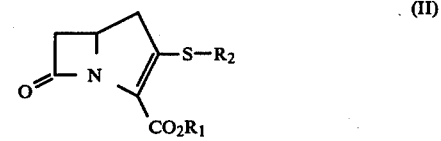

wherein:

$R_1$ is a group such that $CO_2R_1$ is a carboxylic acid group or a salt or ester thereof; and $R_2$ is a phenyl group or a phenyl group substituted by one to four groups selected from lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$ or $CO_2R_{10}$ where $R_3$ is lower alkyl, benzyl, fluorobenzyl, chlorobenzyl, bromobenzyl or nitrobenzyl and $CO_2R_{10}$ is carboxyl or a salt thereof, not more than three such groups being selected from fluorine, chlorine, bromine, CN, $NO_2$, $NH_2$, $COR_3$ or $CO_2R_3$ and not more than two such groups being selected from CN, $NO_2$ and $NH_2$.

66 Claims, No Drawings

SYNTHETIC β-LACTAM COMPOUNDS, A PROCESS FOR THEIR PREPARATION AND COMPOSITIONS CONTAINING THEM

The present invention relates to β-lactam antibacterials, to a process for their preparation and to compositions containing them. British Pat. No. 1483142 and J. Chem. Soc., Chem. Comm., 1977, 523 disclose that the compound of the formula (I).

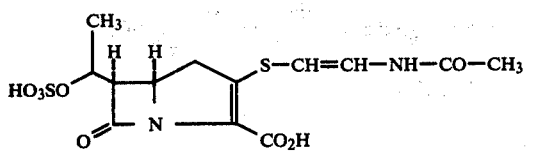

and its salts may be obtained by fermentation of strains of *Streptomyces olivaceus*. We have now found that a distinct class of synthetic antibacterial agents which contain a β-lactam ring fused to a pyrroline ring may be prepared.

Accordingly, the present invention provides the compounds of the formula (II):

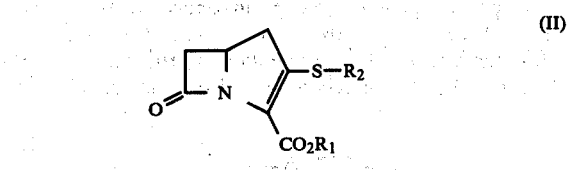

wherein:
  $R_1$ is a group such that $CO_2R_1$ is a carboxylic acid group or a salt or ester thereof; and
  $R_2$ is a phenyl group or a phenyl group substituted by one to four groups selected from lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$ or $CO_2R_{10}$ where $R_3$ is lower alkyl, benzyl, fluorobenzyl, chlorobenzyl, bromobenzyl or nitrobenzyl and $CO_2R_{10}$ is carboxyl or a salt thereof, not more than three such groups being selected from fluorine, chlorine, bromine, CN, $NO_2$, $NH_2$, $COR_3$ or $CO_2R_3$ and not more than two such groups being selected from CN, $NO_2$ or $NH_2$.

An apt group of compounds within formula (II) includes those wherein:
  $R_1$ is a group such that $CO_2R_1$ is a carboxylic acid group or a salt or ester thereof; and
  $R_2$ is a phenyl group or a phenyl group substituted by one or two groups selected from lower alkyl, fluorine, chlorine, bromine, CN, $NO_2$, $COR_3$, $OR_3$, $NHCOR_3$, $NHCO_2R_3$, or $CO_2R_3$ where $R_3$ is a lower alkyl or benzyl group.

When used herein the term "lower" means that the group so described contains 1–4 carbon atoms.

A further apt group of compounds within formula (II) includes those wherein:
  $R_1$ is a group such that $CO_2R_1$ is an ester group; and
  $R_2$ is a phenyl group or a phenyl group substituted by one or two groups selected from fluorine, chlorine, bromine, CN, $NO_2$, $COR_3$, $OR_3$, $NHCOR_3$, $NHCO_2R_3$ or $CO_2R_3$ where $R_3$ is a lower alkyl or benzyl group.

Suitable esterifying groups $R_1$ include alkyl groups of up to 12 carbon atoms, alkenyl groups of up to 12 carbon atoms, alkynyl groups of up to 12 carbon atoms, phenyl or benzyl groups or any of the aforesaid inertly substituted by lower alkoxyl, lower acyloxyl, halogen, nitro or the like group. Used herein 'inertly substituted' means that the resulting group is stable and will not undergo rapid decomposition.

Particularly suitable esterifying groups $R_1$ include lower alkyl groups optionally substituted by lower alkoxyl, the benzyl group optionally substituted by lower alkoxyl, nitro, chloro or the like, and those groups which are known to give rise to rapid in-vivo hydrolysis in penicillin esters.

Certain preferred esterifying groups $R_1$ include methyl, ethyl, methoxymethyl, 2-methoxyethyl, benzyl, methoxybenzyl, nitrobenzyl and the like.

Other particularly preferred esterifying groups $R_1$ include those which give rise to in-vivo hydrolysable esters such as acetoxymethyl, pivaloyloxymethyl, α-ethoxycarbonyloxyethyl, phthalidyl and the like. A preferred group $R_1$ of those giving rise to in-vivo hydrolysable esters is the phthalidyl group.

Preferred groups $R_1$ are those such that $CO_2R_1$ is a carboxylic acid salt.

The group $CO_2R_{10}$ may also be a carboxylic acid salt.

When $CO_2R_1$ is a carboxylic acid salt in compounds of the formula (II) also containing the group $CO_2R_{10}$, then $CO_2R_{10}$ is usually also a carboxylic acid salt, and normally $R_1$ and $R_{10}$ are like cations.

Typical of salts of compounds of formula (II) are conventional pharmaceutically acceptable salts such as the alkali metal and alkaline earth metal salts, in particular the sodium, potassium, calcium and magnesium salts; ammonium and substituted ammonium salts, for example the t-butylamine salt.

Particularly suitable salts are the potassium and sodium salts, especially the sodium salts.

Suitably $R_2$ is a phenyl group, optionally mono-substituted.

Suitable groups $R_2$ include the phenyl, p-chlorophenyl, m-chlorophenyl, p-nitrophenyl, m-nitrophenyl, p-ethoxycarbonylphenyl, p-fluorophenyl, p-methylphenyl, p-aminophenyl, p-acetamidophenyl, p-(4'-nitrobenzyloxycarbonylamino)phenyl, p-methoxyphenyl and like groups.

The compounds of the formula (II) are most easily provided as mixtures of those having the R- and S-configuration at C-5 i.e. the 5R and 5S forms (For example formula (III):

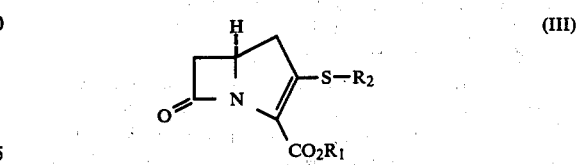

depicts the S-configuration). However this invention also provides the separate 5R and 5S forms.

A preferred sub-group of compounds within formula (II) is of formula (IV):

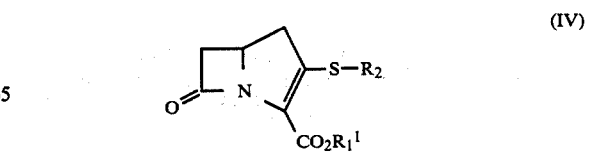

wherein:
R$^1_1$ is a group such that CO$_2$R$^1_1$ is an ester group of the type which is known to undergo rapid in-vivo hydrolysis in penicillin esters; and
R$_2$ is as defined in formula (II).

Suitable groups R$^1_1$ include acetoxymethyl, pivaloyloxymethyl, α-ethoxycarbonyloxyethyl, phthalidyl and the like. R$^1_1$ is preferably phthalidyl.

Suitable groups R$_2$ are as so described under formula (II).

A second preferred sub-group of compounds within formula (II) is of formula (V):

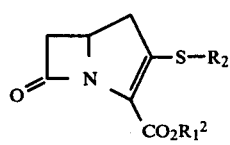

wherein:
R$^2_1$ is a group such that the compound of formula (V) is a carboxylic acid salt; and
R$_2$ is as defined in formula (II).

Particularly suitable salts are the potassium and sodium salts, especially the sodium salts.

Suitable groups R$_2$ are as so described under formula (II).

A sub-group of compounds within formula (II) of interest is of formula (VI):

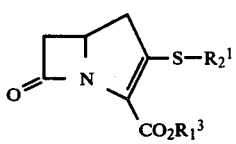

wherein:
R$^3_1$ and R$^1_2$ are as in the Examples hereinafter.
A suitable group R$^3_1$ is tert-butyl.
Another suitable group R$^3_1$ is methyl.
An additional suitable group R$^3_1$ is benzyl.
Similarly, a suitable group R$^3_1$ is p-nitrobenzyl.
One more suitable group R$^3_1$ is phthalidyl.
A further suitable group R$^3_1$ is pivaloyloxymethyl.
Yet a further suitable group R$^3_1$ is sodium.
p-Nitrobenzyl is a preferred group R$^3_1$.
Phthalidyl is also a preferred group R$^3_1$.
Sodium is another preferred group R$^3_1$.
A suitable group R$^1_2$ is p-acetamidophenyl.
An additional suitable group R$^1_2$ is phenyl.
Similarly, a suitable group R$^1_2$ is p-nitrophenyl.
One more suitable group R$^1_2$ is p-aminophenyl.
A further suitable group R$^1_2$ is p-(4'-nitrobenzyloxycarbonylamino)phenyl.

A reaction sequence leading to the compounds of this invention is as follows:

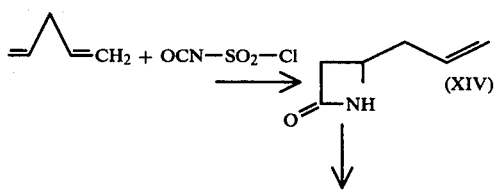

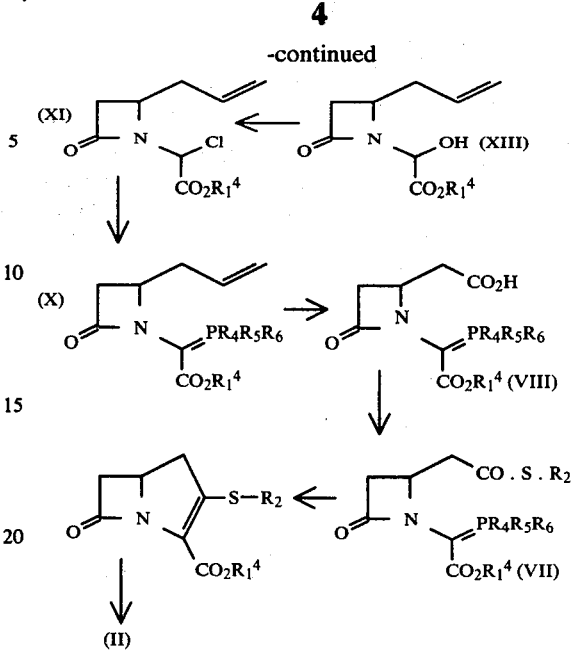

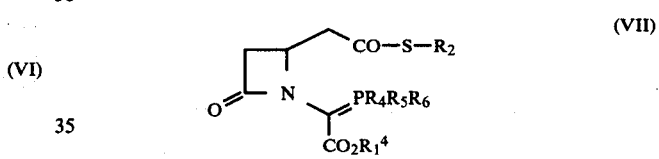

The process provided by this invention for the preparation of the compounds of the formula (II) comprises (a) the ring closing elimination of the elements of O=PR$_4$R$_5$R$_6$ from a compound of the formula (VII):

wherein CO$_2$R$^4_1$ is an ester group, as defined in relation to formula (II) and R$_4$, R$_5$ and R$_6$ are each lower alkyl, phenyl or diloweralkylamino groups, (b) thereafter isolating the ester of the formula (II) so formed, (c) where desired de-esterifying the ester to form a free acid or its salt, (d) and thereafter optionally salifying or esterifying the free carboxylic acid so formed, or (e) thereafter optionally converting the salt so formed into a free carboxylic acid, an ester or another salt.

Most suitably R$_4$, R$_5$ and R$_6$ are each phenyl groups.

The ring closure is normally brought about by heating the compound of the formula (VII) in an inert solvent; for example temperatures of 90°–120° C. and more suitably 100°–110° C. may be employed in a solvent such as toluene or the like. The reation is best carried out under dry conditions under an inert gas.

The ester of the compound (II) produced may be isolated by any standard method such as fractional crystal-lisation or chromatography. We have found that it is most convenient to separate the desired product by column chromatography.

Any convenient ester may be used in the process of this invention. Since it is frequently desirable to form a salt of compounds (II), the ester employed is preferably one which is readily converted to the parent acid or its salt by mild methods of hydrogenolysis. In a further aspect therefore the invention includes a process for preparing a salt or free acid of a compound (II) which process comprises de-esterifying an ester of a compound of formula (II). Particularly suitable esters for use in this process include benzyl esters, optionally substituted in the para position by a lower alkoxy, or nitro group or a halogen atom.

A preferred ester for use in this process is the p-nitrobenzyl ester.

Esters of compounds (II) may be de-esterified by conventional methods of hydrogenolysis.

Suitable methods include hydrogenation in the presence of a transition metal catalyst. The pressure of hydrogen used in the reaction may be low, medium or high but in general an approximately atmospheric or slightly superatmospheric pressure of hydrogen is preferred. The transition metal catalyst employed is preferably palladium on charcoal or on calcium carbonate. The hydrogenation may be effected in a suitable solvent in which the ester is soluble such as aqueous dioxan or the like. If this hydrogenation is carried out in the presence of a base then a salt of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$ and the like. If no base is present then hydrogenation leads to the preparation of an acid within formula (II) which may then be neutralised if desired to yield a salt. Suitable bases which may be used to neutralise acids within formula (II) include LiOH, NaOH, NaHCO$_3$, KOH, $Ca(OH)_2$ and $Ba(OH)_2$.

The salts of acids (II) may be converted to esters in conventional manner, for example by reaction with a reactive halide such as bromophthalide in solution in dimethylformamide or like solvent.

The substituent group or groups within the group $R_2$ in the compounds of formula (II) may be varied by conventional reactions. Thus for example when a substituent is a nitro group it may be reduced in a conventional manner to an amino group, for example by catalysed hydrogenation. Similarly an amino group may be acylated to give a substituted amido group, for example by treatment with an acyl halide in the presence of an organic base. Substituents $NHCO_2R_3$ where $R_3$ is a benzyl group substituted as hereinbefore described may be converted to amino groups, for example by hydrogenolysis.

Compounds of the formula (II) wherein the group $R_2$ contains one or more substituents $CO_2R_{10}$ as hereinbefore defined are preferably prepared from corresponding compounds of the formula (VII) wherein $R_2$ contains corresponding substituents $CO_2R_3^1$ where $CO_2R_3^1$ is a group readily convertible to a group $CO_2R_{10}$ by hydrogenolysis. Suitable and preferred hydrogenolysis methods and esters therefor are those so described hereinbefore for the de-esterification of $CO_2R_1$ ester groups.

The compound of the formula (VII) may be prepared by the reaction of a corresponding compound of the formula (VIII):

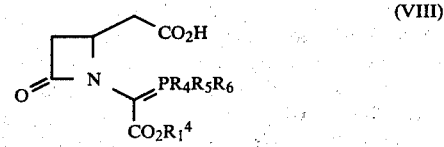

(VIII)

wherein $R_4$, $R_5$ and $R_6$ are as defined in relation to formula (VII) with a diloweralkylphosphorochloridate and a triloweralkylamine followed by reaction with a derivative of the formula (IX):

$$L^{\oplus \ominus}S-R_2 \quad (IX)$$

where $L^\oplus$ is a sodium or thallium (I) cation or an ammonium ion substituted by up to three organic groups, and $R_2$ is as defined in relation to formula (II).

When $L^\oplus$ is a substituted ammonium ion, it is preferably a tertiary ammonium ion, such as the triethylammonium ion. It is conveniently generated in situ to the reaction of a compound of the formula $HSR_2$ with an amine, preferably a tertiary amine.

Favourably $L^{61}$ is a thallium (I) cation. Favourably $L^\oplus$ is a sodium cation.

A particularly suitable diloweralkylphosphorochloridate is diethylphosphorochloridate.

A particularly suitable triloweralkylamine is triethylamine.

The reaction is generally carried out in an inert organic solvent such as tetrahydrofuran at a non-extreme temperature such as 0° to 40° C., for example 15°–25° C.

The compound of the formula (VIII) may be prepared by the reaction of the compound of the formula (X):

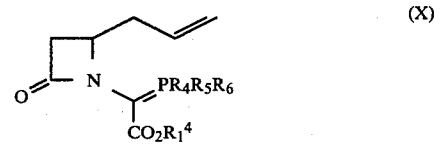

(X)

wherein $R^4_1$, $R_4$, $R_5$ and $R_6$ are as defined in relation to formula (VIII) with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The compound of the formula (X) may be prepared from the corresponding compound of the formula (XI):

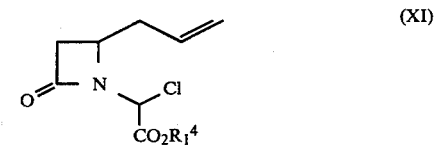

(XI)

wherein $R^4_1$ is as defined in relation to formula (X) with a phosphine of the formula (XII):

$$PR_4R_5R_6 \quad (XII)$$

where $R_4$, $R_5$ and $R_6$ are as defined in relation to formula (X).

This reaction is normally effected in the presence of at least one equivalent of a base of relatively low nucleophilicity such as 2,6-lutidine at an ambient temperature in a dry solvent such as dioxan, tetrahydrofuran or the like.

The compound of the formula (XI) may be prepared from the corresponding carbinol of the formula (XIII):

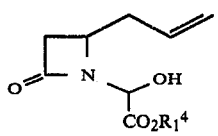

(XIII)

wherein $R^4_1$ is as defined in relation to formula (XI) by reaction with thionyl chloride.

This reaction is also normally effected in the presence of at least one equivalent of a base of relatively low nucleophilicity in a dry solvent such as dioxan or tetrahydrofuran but in this intance the reaction is performed at a depressed temperature, for example −30° to −10° C.

The preceding carbinol may be prepared by the reaction of a compound of the formula (XIV):

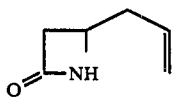

(XIV)

with a glyoxylic acid ester of the formula (XV):

(XV)

wherein $R^4_1$ is as defined in relation to formula (VII).

Normally this reaction is carried out in an inert solvent at an elevated temperature, for example in dry benzene under reflux.

The compound of the formula (XIV) may be prepared as described in Description 1 hereinafter.

The present invention provides the compounds of the formulae (VII) and (VIII), as useful intermediates. The process for the preparation of these compounds also forms part of this invention.

The present invention also provides a pharmaceutical composition which comprises a compound of the formula (II) as hereinbefore defined and a pharmaceutically acceptable carrier.

The composition of the invention includes those in a form adapted for oral, topical or parenteral use and may be used for the treatment of bacterial infection in domestic animals or humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibacterial agents.

Preferably the compound of the formula (II) present in such compositions will be in-vivo hydrolysable to the parent acid or its salt.

The composition of this invention may beneficially also comprise a penicillin or cephalosporin. Certain particularly suitable penicillin for use in these compositions include amoxycillin trihydrate and sodium amoxycillin.

The present invention also provides a method of treatment and/or prophylaxis of bacterial infections in human beings or domestic animals, which method comprises the administration to the sufferer of an effective amount of a compound of the formula (II).

The following Examples illustrate this invention. The following Descriptions relate to the preparation of useful intermediates.

DESCRIPTION 1

4-Allyl-1-(1-tert-butyloxycarbonyl-1-triphenylphosphoranylidenemethyl)azetidine-2-one (i) Preparation of 4-allyl azetidin-2-one

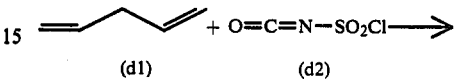

(d1) (d2)

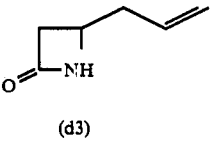

(d3)

1,4 Pentadiene(d1) (30 g) and chlorosulphonyl isocyanate (d2)(35.4 ml) were mixed and allowed to stand at room temperature for 3 days, in a pressure bottle. The thick, dark syrup obtained was diluted with methylene chloride (500 ml) and added dropwise to a stirred solution of sodium sulphite (66 g) in water (240 ml). The pH was maintained between 6.5 and 7.5 by the addition of 10% aqueous potassium hydroxide (600 ml in total). The lower organic phase was separated and the aqueous phase extracted (×2) with ethyl acetate. The combined organic extracts were dried over magnesium sulphate, filtered, and evaporated to give the crude azetidinone (d3) as a red oil (16.05 g). This was sufficiently pure for use in subsequent reactions e.g. Description 1 (ii), but could be further purified by distillation b.p. 76°–80°/0.2 mm.$\nu_{max}$ (CHCl$_3$) 3490, 1770 (strong), 1650 (weak)cm$^{-1}$. δ ppm (CDCl$_3$) 2.39 (2H, t, J 6 Hz, CH$_2$), 2.61 (1H, ddd, J 14 Hz, 2 Hz, 1.5 Hz, collapsing with D$_2$O to dd, J 14 Hz, 2 Hz, C3—H), 3.10 (1H, ddd, J 14 Hz, 5 Hz, 2 Hz, collapsing with D$_2$O to dd, J 14 Hz, 5 Hz, C3—H), 3.55–3.91 (1H, m C4—H), 4.98–6.21 (3H, complex pattern, CH=CH$_2$), 6.67 (1H, broad s, exch. D$_2$O) (Found: M, 111.0683. C$_6$H$_9$NO requires M, 111.0684).

(ii) Preparation of 4-allyl-1-(1'-hydroxy-1'-tert-butyloxycarbonylmethyl)azetidin-2-one

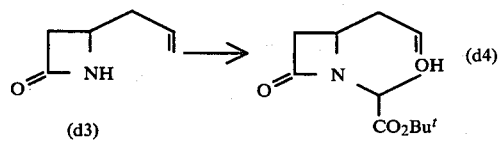

(d4)

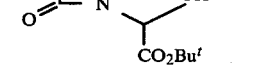

(d3)

tert-Butyl glyoxylate hydrate (6.22 g) in benzene (120 ml) was refluxed for 1 hour in a Dean-Stark apparatus to remove the water. The azetidinone (d3)(2.31 g) was then added and the reaction mixture refluxed for 4 hours. Chromatography of the crude product as in Description 3(i) gave the alcohol (d4) as a pale yellow oil (4.48 g). $\nu_{max}$ (CHCH$_3$) 3490, 1755, 1735, 1640 (weak)cm$^{-1}$ δ ppm (CDCl$_3$) 1.50 (9H, s, Bu-$^t$), 2.20–3.25 [4H, 2.66 (1H, dd, J 3 Hz, 14 Hz, C3—H), and 3.09 (1H, dd, J 14 Hz, 5 Hz, C3—H) obscuring 2H, CH$_2$]; 3.68–4.10 (1H, m, C4—H), 4.47 (1H, broad s, exch. D₂O OH); 4.98-5.37 (3H, m, sharpening with D₂O), 5.52-6.23 (1H, m, CH=CH₂). M+ at m/e 241 and (m/e+1).

(iii) Preparation of 4-allyl-1-(1'-tert-butyloxycarbonyl-1'-triphenylphosphoranylidenemethyl)azetidin-2-one

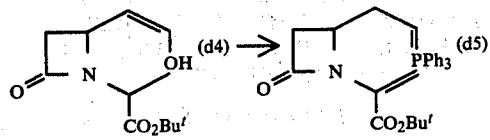

A stirred solution of the alcohol (d4) (4.2 g) in dry tetrahydrofuran (120 ml) under argon, was cooled to −20°, and treated with lutidine (4.03 ml) in tetrahydrofuran (15 ml). Thionyl chloride (2.54 ml) in tetrahydrofuran (15 ml) was added dropwise. After allowing to reach 0° over 30 minutes, the solution was filtered, the lutidine hydrochloride being washed with toluene.

The combined filtrate and washings were evaporated to dryness. The residue was taken up in dry dioxan (100 ml) and treated with lutidine (4.03 ml) and triphenylphosphine (9.1 g). After stirring at room temperature overnight, the phosphorane (d5) was isolated as in Description 3 (ii) and obtained as white crystals (4.62 g) from ether mp. 188°-9°, $\nu_{max}$ (CHCl₃) 1730, 1638, 1610 cm⁻¹ (Found: C, 74.1; H, 6.8; N, 3.0, P, 6.2% C₃₀H₃₂NO₃P requires C, 74.2, H, 6.6, N, 2.9, P, 6.4%).

DESCRIPTION 2

4-Allyl-1-(1'-methoxycarbonyl-1'-triphenylphosphoranylidenemethyl)azetidin-2-one (i) Preparation of 4-allyl-1-(1'-hydroxy-1'-methoxycarbonylmethyl)azetidin-2-one

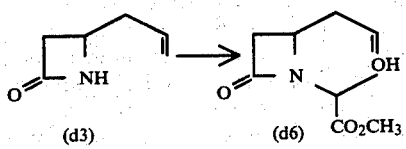

Methyl glyoxylate hydrate (9.75 g) in benzene (500 ml) was refluxed for 1 hour in a Dean-Stark apparatus to remove the water. The azetidinone (d3) (2.68 g) was then added and the reaction mixture refluxed for 2 hours. A further portion of the azetidinone (1.34 g) (d3) was then introduced, and refluxing continued for 3 hours. Chromatography of the crude product as in description 3 (i) gave the alcohol (d6) as a pale yellow oil (5.33 g). $\nu_{max}$ (CHCl₃) 3500, 3350 (broad), 1760-1740 (strong), 1640 (weak) cm⁻¹. δ ppm (CDCl₃) 2.24-2.90 (3H, m, including [1H, dd, J 3 Hz, 14.5 Hz at δ 2.63]), 3.11 (1H, dd, J 4.5 Hz, 14.5 Hz), 3.72-4.42 (5H, including [3H, s, at δ 3.90], 1H, exch. D₂O), 5.00-6.29 (4H, m including [1H, s, at δ 5.48]).

(ii) Preparation of 4-allyl-1-(1'-methoxycarbonyl-1'-triphenylphosphoranylidene-methyl)azetidin-2-one

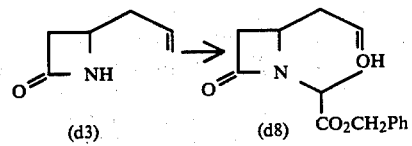

A stirred solution of the alcohol (d6) (5.23 g) in dry tetrahydrofuran (150 ml) under argon, was cooled to −20°, and treated with lutidine (6.06 ml) in tetrahydrofuran (20 ml). Thionyl chloride (3.83 ml) in tetrahydrofuran (20 ml) was added dropwise. After allowing to reach 0° over 20 minutes, the solution was filtered, the lutidine hydrochloride being washed with toluene.

The combined filtrate and washings were evaporated to dryness. The residue was taken up in dry dioxan (150 ml) and treated with lutidine (6.06 ml) and triphenylphosphine (13.7 g). After stirring at room temperature, overnight, the phosphorane (d7) was isolated as in Description 3 (ii) and obtained as white crystals (7.3 g) from ether m.p. 208°-212°. $\nu_{max}$ (CHCl₃) 1738, 1640, 1620 cm⁻¹ (Found: C, 72.6; H, 5.9; N, 3.0%. C₂₇H₂₆NO₃P requires C, 73.1; H, 5.9; N, 3.2%).

DESCRIPTION 3

(i) 4-Allyl-1-(1'-benzyloxycarbonyl-1'-triphenylphosphoranylidenemethyl)azetidin-2-one

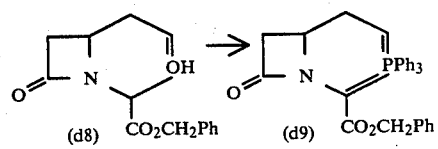

Benzyl glyoxylate hydrate (6 g) in benzene (120 ml) was refluxed for 0.5 hours in a Dean-Stark apparatus to remove the water. The azetidinone (d3) (2.13 g) was added and the reaction mixture refluxed for 4 hours. The solution was cooled, evaporated, and chromatographed on silica gel, eluting with ethyl acetate-petroleum ether mixtures to give a colourless oil (5.6 g) consisting mainly of the isomers of (d8) and sufficiently pure for use in subsequent reactions. Rechromatography of a small portion of this oil, eluting with chloroform gave (d8) as an oil. $\nu_{max}$ (CHCl₃) 3420, 1750 (strong), 1640 (weak) cm⁻¹. δ ppm (CDCl₃) 1.90-3.05 [4H, m, including δ 2.53 (1H, dd, J 15 Hz, 2 Hz, C3—H), 2.92 (1H, dd, J, 15 Hz, 5 Hz, C3—H), obscuring 2H, CH₂], 4.52 (1H, broad s, exch. D₂O, —OH), 4.85-5.90 [6H, m, including δ 5.40 (1H, broad, collapsing with D₂O to singlet, H—C—OH)+complex pattern for CH₂Ph and CH=CH₂], 7.29 (5H, s).

(ii) Preparation of 4-allyl-1-(1'-benzyloxycarbonyl-1'-triphenylphosphoranylidenemethyl)azetidin-2-one.

A stirred solution of the alcohol (d8) (6.6 g) in dry tetrahydrofuran (200 ml), under argon, was cooled to −20°, and treated with lutidine (5.13 g) in tetrahydrofuran (10 ml). Thionyl chloride (5.70 g) in tetrahydrofuran (20 ml) was added dropwise. After allowing to reach 0° C. over 20 minutes, the precipitated solid was filtered off, washing with dry toluene.

The combined filtrate and washings were evaporated to dryness and the residue taken up in dry toluene, filtered and evaporated. The gum obtained was taken up in dioxan (200 ml) and treated with triphenylphosphine (12.6 g) and lutidine (5.53 ml). After stirring under argon at room temperature for 3 hours and standing overnight, the precipitated solid was filtered off. The filtrate was evaporated to dryness. Chromatography on silica gel eluting with ethyl acetate-petroleum ether mixtures, gave the required phosphorane, initially as a foam, which crystallised from ether (5.7 g) m.p. 150°–6° C. $\nu_{max}$ (CHCl$_3$) 1730, 1638, 1610 cm$^{-1}$.

DESCRIPTION 4

4-Allyl-1-(1'-p-nitrobenzyloxycarbonyl-1'-triphenyl-phosphoranylidenemethyl)azetidin-2-one.

(i) Preparation of allyl-1-(1'-hydroxy-1'-p-nitrobenzyloxycarbonylmethyl)azetidin-2-one

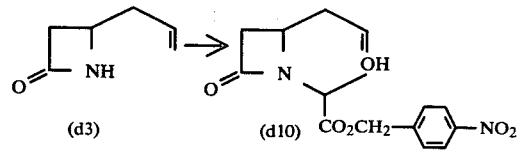

p-Nitrobenzylglyoxylate hydrate (6.8 g) in benzene (120 ml) was refluxed for one hour with removal of water (Dean-Stark). The azetidinone (d3) (3 g) was added and the mixture refluxed for two hours. The solution was cooled, the solvent was evaporated, and the residue was chromatographed. Elution with 80% ethyl acetate/petroleum ether (60°–80° C.) gave the product. The product was rechromatographed to complete purification and collected as an oil (3.2 g) (37%) $\nu_{max}$(CHCl$_3$) 3,500 (OH), 1755 (br), 1530, 1355 cm$^{-1}$. $\delta$ ppm (CDCl$_3$) 2.39 (2H, m CH$_2$CH=CH$_2$), 2.61 (1H, dd, J 16H, 4 Hz, C3—H), 3.05 (1H, dd, J 16 Hz, 6 Hz, C3—H), 3.92 (1H, m, C4—H), 4.63 (1H, m, collapsing to a singlet on D$_2$O exchange, CH—OH), 4.80 to 5.80 (6H, complex pattern including CH$_2$PhNO$_2$ at 5.35, OH [exchangeable] and CH=CH$_2$) 7.56 and 8.23 (4H, ABq, J 8 Hz, aromatics).

(ii) Preparation of 4-allyl-1-(1'-p-nitrobenzyloxycarbonyl-1'-triphenylphosphoranylidenemethyl) azetidin-2-one

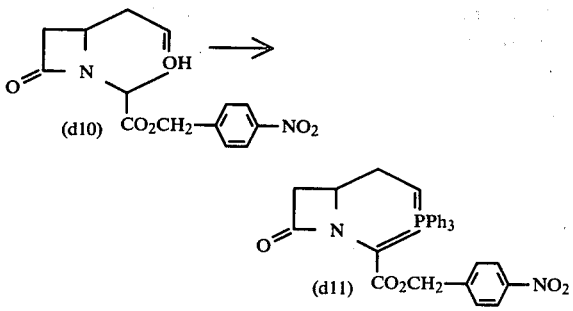

A stirred solution of the alcohol (d10) (1.6 g) in dry THF (100 ml) was treated with 2,6-lutidine (1.07 g) and thionyl chloride (1.19 g) in THF (20 ml) at −20°, and stirring was continued for 20 minutes. The mixture was filtered, the solvent was evaporated, and the residue was azeotroped twice with toluene. It was dissolved in dioxan (100 ml), and 2,6-lutidine (1.07 g) and triphenylphosphine (2.62 g) were added. The reaction was stirred overnight at RT and filtered. The solvent was evaporated, and the residue was chromatographed. After decolourising with charcoal (ethanol/ethyl acetate) and trituration of the residue from the evaporated solution with ether, (d11) was obtained as a yellow solid (1.5 g; 53%) m.p. 182°–3° $\nu_{max}$(CHCl$_3$) 1740, 1620, 1525, 1355 cm$^{-1}$. (Found: C, 70.26; H, 5.33; N, 4.80. C$_{33}$H$_{29}$N$_2$O$_5$P requires C, 70.21; H, 5.14; N, 4.96%).

DESCRIPTION 5

4-Allyl-1-(1'-pivaloyloxymethoxycarbonyl-1'-triphenylphosphoranylidenemethyl)azetidine-2-one

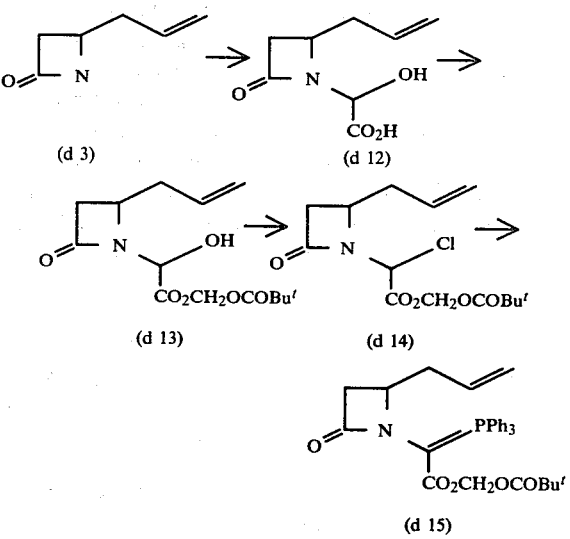

4-Allylazetidin-2-one (d 3) (2.0 g) and glyoxylic acid monohydrate (1.75 g) were stirred together in dry dimethylformamide (10 ml) for 6 hours in the presence of 4A molecular sieves. The mixture was then cooled in an ice bath and powdered potassium carbonate (1.31 g) was added. It was allowed to warm to room temperature and stirred for 5 minutes prior to adding pivaloyloxymethyl bromide (5.3 g). The reaction was stirred overnight and then poured into a mixture of N/10 hydrochloric acid (80 ml) and ethyl acetate (80 ml). The organic phase was separated and the aqueous solution washed with further ethyl acetate (50 ml). The ethyl acetate solutions were combined, washed with saturated aqueous sodium bicarbonate, then brine and dried over sodium sulphate. It was concentrated in vacuo to give the crude ester (d 13) as a yellow oil (4.7 g).

The crude ester (d 13) (4.7 g) was dissolved in dry tetrahydrofuran (80 ml) and stirred at −20° under argon. It was treated with 2,6-lutidine (3.7 ml) followed over a period of 5 minutes by a solution of thionyl chloride (2.3 ml) in tetrahydrofuran (20 ml). The reaction was allowed to warm to ambient temperature over a period of ½ hour and then filtered. The solid was washed with dry toluene and the combined filtrates concentrated under reduced pressure. The vestigial thionyl chloride was removed by two further evaporations from toluene to give the chloride (d14) as a brown oil.

The chloride (d 14) was dissolved in dry dioxane (80 ml) and treated with triphenylphosphine (8.2 g) and 2,6-lutidine (3.7 ml). The reaction mixture was stirred overnight and then filtered; the filtrate concentrated and re-dissolved in ethyl acetate (100 ml). This solution was washed free of base with N/10 hydrochloric acid (ca 100 ml) and then washed with brine and dried over sodium sulphate. The solution was concentrated and then chromatographed on silica gel 60 (<230 mesh) eluting with ethyl acetate/60°-80° petroleum ether 7:3 to give a foam. This was dissolved in diethyl ether (20 ml) and a white solid rapidly crystallised out. This was 4-allyl-1-(1'-pivaloyloxymethoxycarbonyl-1'-triphenyl-phosphoranylidenemethyl)azetidine-2-one (d 15) which was obtained in a yield of 3.06 g; m.p. 140°-142° (ethyl acetate/60°-80° petroleum ether; $\nu_{max}$ (CHCl$_3$) 2980, 1740 and 1635 cm$^{-1}$.

EXAMPLE 1 t-Butyl 7-oxo-3-p-nitrophenylthio-1-azabicyclo-[3.2.0]-hept-2-ene-2-carboxylate (a) Preparation of 1-(1'-t-butoxycarbonyl-1'-triphenylphosphoranylidenemethyl)-4-carboxymethylazetidin-2-one

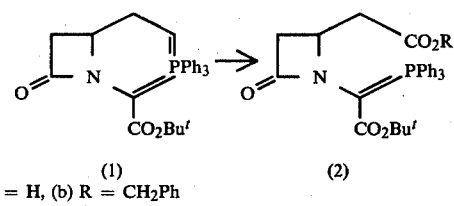

(1)            (2)
(a) R = H, (b) R = CH$_2$Ph

The phosphorane (1) (Prepared as Description 1) (2 g) was dissolved in dry methylene chloride (100 ml) and treated with trifluoroacetic acid (3.2 ml). The solution was cooled to −70° C. and ozonised until the solution turned blue. Excess ozone was removed by passing through argon and m-chloroperbenzoic acid (720 mg) in methylene chloride (20 ml) was added. The mixture was allowed to reach RT and stirred overnight. The solvent was evaporated and the residue chromatographed on Merck Kieselgel 60 (<230 mesh). Elution with 50% ethanol/ethyl acetate gave the phosphorane-acid (2a) as a colourless foam which crystallised from ethyl acetate/ether (1.6 g) as a mixture of zwitterion and trifluoroacetic acid salt, $\nu_{max}$ 1770, 1750, 1670, 1590 cm$^{-1}$.

The product (1.6 g) was taken up in CHCl$_3$ (50 ml) and stirred with basic alumina (4 g) overnight. The solution was filtered, the solvent evaporated and the residue triturated with ether to yield the phosphorane-acid (2a) as a white solid (0.9 g) mp 141°-3° C. $\nu_{max}$ (CHCl$_2$) 1750, 1595, 1590 cm$^{-1}$.

The acid (2a) was further characterised by treatment with benzyl bromide and potassium carbonate in dimethylformamide to give the benzyl ester (2b), obtained as white crystals (ex ether) m.p. 176.5°-178° C. $\sigma_{max}$ (CHCl$_3$) 1735, 1640, 1610 cm$^{-1}$. (Found: C, 72.20; H, 6.59; N, 2.28; C$_{36}$H$_{36}$NO$_5$P requires C, 72.83; H, 6.11; N, 2.36%).

(b) Preparation of 1-(1'-t-butoxycarbonyl-1'-triphenylphosphoranylidenemethyl)-4-(p-nitrophenylthiocarbonylmethyl)azetidin-2-one

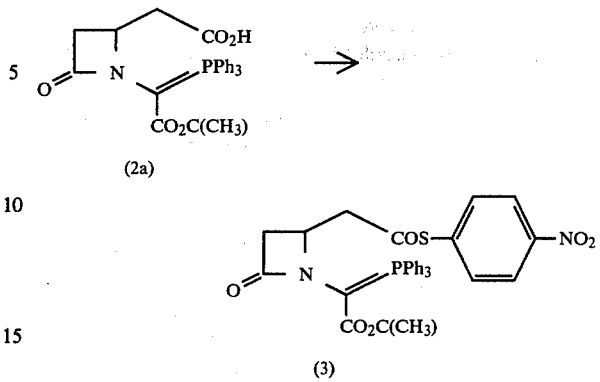

(2a)

(3)

The acid (2a) (1.06 g; 2 mmol) and Et$_3$N (222 mg; 2.2 mmole) were stirred in dry THF (20 ml) at RT. A solution of diethyl phosphorochloridate (363 mg; 2.2 mmol) in THF (5 ml) was added dropwise under argon at RT and the mixture stirred for 3h. The solution was filtered and to the filtrate was added (787 mg; 2.2 mmol) of thallium (I) p-nitrophenylthiolate. The mixture was stirred overnight, filtered and the filtrate evaporated. Chromatography on Merck Kieselgel 60 (−230 mesh) using ethyl acetate—petrol yielded the product (3) as an oil which crystallised from ethyl acetate/petrol as a light yellow crystalline solid (570 mg; 56% mp 115°-6° C. $\nu_{max}$ (CHCl$_3$) 1740, 1720 (sh), 1640 cm$^{-1}$ (Found: C, 65.82; H, 5.40; N, 4.32. C$_{35}$H$_{33}$N$_2$O$_6$SP requires C, 65.62; H, 5.16; N, 4.38%).

(c) Preparation of t-butyl 7-oxo-3-p-nitrophenylthio-1-azabicyclo-[3.2.0]hept-2-ene-2-carboxylate

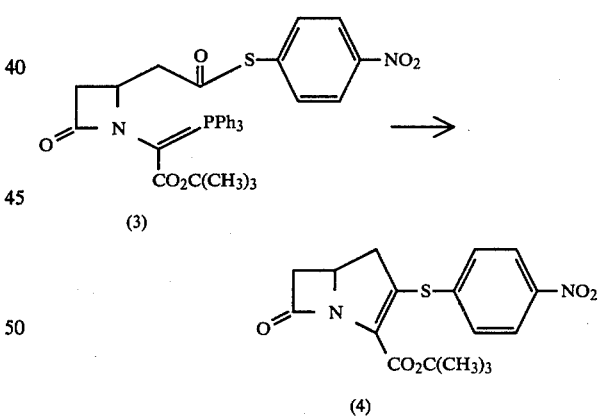

(3)

(4)

The phosphorane (3) (128 mg) was heated in refluxing toluene (50 ml) for 15 min. The solvent was evaporated and the residue chromatographed on Merck Kieselgel 60 (<230 mesh) to yield 15 mg of crude product. Re-chromatography yielded the title product (4) as a light yellow crystalline solid from ethyl acetate/petrol mp 148°-50° C. $\nu_{max}$ (CHCl$_3$) 1790, 1710, 1695, 1525, 1345 cm$^{-1}$. δ ppm (CDCl$_3$) 1.57 (9H, s, CO$_2$C(C$\underline{H}_3$)$_3$), 2.70 (2H, d, J 9.5 Hz, C4—C$\underline{H}_2$), 2.83 (1H, dd, J 17, 3 Hz, C6—$\underline{H}$ trans), 3.43 (1H, dd, J 17, 5 Hz, C6—$\underline{H}$, cis), 4.12 (1H, m, C5—$\underline{H}$), 7.62 and 8.17 (4H, ABq, j 9 Hz aromatic protons), $\lambda_{max}$ (EtOH) 265 nm ($\epsilon$=14,300) 309 nm ($\epsilon$=17,300), 346 nm (sh) ($\epsilon$=13,700).

EXAMPLE 2 t-Butyl 7-oxo-3-phenylthio-1-azabicyclo[3.2.0]hept-2-ene-2-carboxylate.

(a) Preparation of 1(1'-t-butoxycarbonyl-1'-triphenylphosphoranylidenemethyl)-4-(phenylthiocarbonylmethyl)azetidin-2-one

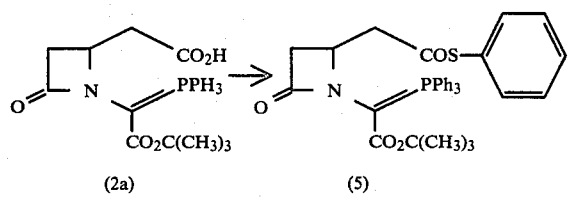

(2a)　　　　　(5)

The acid (2a) (754 mg; 1.5 mmol) was dissolved in dry THF (15 ml) containing Et$_3$N (167 mg; 1.6 mmol) and stirred at RT. A solution of diethylphosphorochloridate (272 mg; 1.6 mmol) in THF (5 ml) was added dropwise to the solution under argon. Stirring was continued for 3h. The solution was filtered, and to the solution was added thallium (I) phenylthiolate (500 mg; 1.6 mmol). Stirring was continued overnight. The solution was filtered, the solvent evaporated and the residue chromatographed on Merck Kieselgel 60 using ethyl acetate-petrol to yield the phosphorane (5) (700 mg) as an oil. trituration with ether gave the phosphorane as a microcrystalline solid (550 mg) mp 152°–5° C. $\nu_{max}$ 1740, 1700, 1640 cm$^{-1}$ (Found: C, 70.74; H, 5.76; N, 2.43. C$_{35}$H$_{34}$NO$_4$SP requires C, 70.59; H, 5.71; N, 2.35%).

(b) Preparation of t butyl-7-oxo-3-phenylthio-1-azabicyclo-[3.2.0]hept-2-ene-2-carboxylate

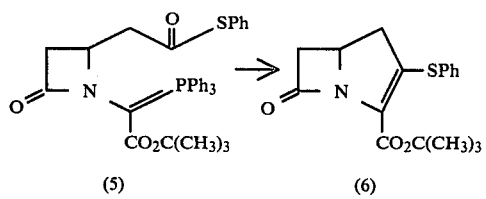

(5)　　　　　(6)

The phosphorane (5) (120 mg) was refluxed in dry toluene (10 ml) under argon for six hours. The solvent was evaporated and the product chromatographed on Merck Kieselgel 60 to yield the title product (6) as the second compound eluted from the column (25 mg; 39%). $\nu_{max}$ (CHCl$_3$) 1785, 1700 cm$^{-1}$. δ ppm (CDCl$_3$) 1.56 (9H, s, CO$_2$C(C$\underline{H}_3$)$_3$), 2.57 (2H, d, J 9 Hz; C4—C$\underline{H}_2$), 2.74 (1H, dd, J 17, 3 Hz, C6—H, trans), 3.32 (1H, dd, J 17, 5 Hz, C6—$\underline{H}$, cis), 3.97 (1H, m. C5—$\underline{H}$), 7.39 (5H, m, Ph), $\nu_{max}$ (EtOH) 313 nm (ε=9,510) (Found: M, 317.1105, C$_{17}$H$_{19}$NO$_3$S requires 317.1085).

EXAMPLE 3

Methyl 7-oxo-3-phenylthio-1-azabicyclo[3.2.0]hept-2-ene-2-carboxylate.

(a) Preparation of 1(1'-methoxycarbonyl-1'-triphenylphosphoranylidenemethyl)-4-carboxymethylazetidine-2-one

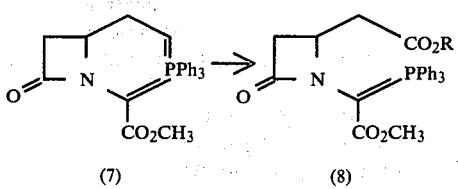

(7)　　　　　(8)

a, R = H
b, R = CH$_2$Ph

The phosphorane (7) (Prepared as in Description 2) (4.47 g) in dry methylene chloride (250 ml), was treated with trifluoroacetic acid (7.7 ml). The solution, cooled to −70° C., was ozonised until it became blue. After passing argon through to remove excess ozone, m-chloroperbenzoic acid (1.74 g) in methylene chloride (50 ml) was added. The stirred mixture was allowed to reach room temperature, and after stirring overnight, was evaporated to dryness. After re-evaporation from dry toluene the residue was chromatographed on Merck Kieselgel 60. Elution with ethyl acetate gave m-chlorobenzoic acid. Further elution with 10% ethanol acetate gave the phosphorane-acid (8a), partially as the trifluoroacetic acid salt, as a yellow foam (2.7 g), $\nu_{max}$ (CH$_2$Cl$_2$) 1770, 1755, 1738, 1705–1675 (several weak peaks), 1585 cm$^{-1}$.

This foam was taken up in dry methylene chloride (70 ml), and stirred with basic alumina (8 g), for 2 hours. Evaporation of the filtered solution gave a foam (3 g). Trituration with ether gave the zwitterionic form of the acid-phosphorane (8a), as a pale yellow solid, which was collected and dried in vacuo (2.35 g) $\nu_{max}$ (CH$_2$Cl$_2$) 1750, 1740, 1590 cm$^{-1}$.

The acid (8a) was characterised by treatment with benzyl bromide and potassium carbonate in dimethylformamide to give the benzyl ester (8b), as white crystals (ex ethyl acetate/petroleum ether), mp 146°–8° C., $\nu_{max}$ (CHCl$_3$) 1740, 1620 cm$^{-1}$ (Found: C, 71.71; H, 5.67; N, 2.44. C$_{33}$H$_{30}$NO$_5$P requires C, 71.87; H, 5.44; N, 2.54%.

(b) Preparation of 1-(1'-methoxycarbonyl-1'-triphenylphosphoranylidenemethyl)-4-(phenylthiocarbonylmethyl)azetidin-2-one

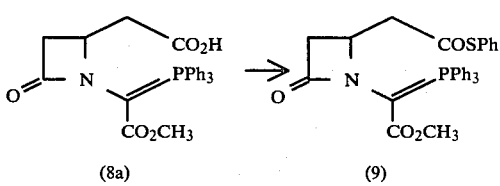

(8a)　　　　　(9)

The acid (8a) (461 mg; 1 mmol) was dissolved in dry THF containing Et$_3$N (110 mg; 1.1 mmol) and stirred at RT whilst a solution of diethylphosphorochloridate (152 mg; 1.1 mmol) in THF (5 ml) was added dropwise at RT under argon. The solution was filtered, and thallium (I) phenylthiolate (345 mg; 1.1 mmol) was added to the filtrate. Stirring was continued overnight, the solution filtered, the solvent evaporated and the residue chromatographed to yield the phosphorane (9) as an oil (400 mg). Trituration with ether yielded the phosphorane as a microcrystalline solid mp 172°–3° C., $\nu_{max}$ 1740, 1700, 1620 cm$^{-1}$ (Found: C, 68.84; H, 5.24; N, 2.33. C$_{32}$H$_{28}$NO$_4$SP requires C, 69.43; H, 5.06; N, 2.53%).

(c) Preparation of methyl 7-oxo-3-phenylthio-1-azabicyclo[3.2.0]hept-2-ene-2-carboxylate

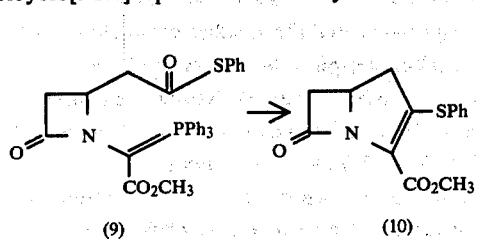

The phosphorane (9) (80 mg) was heated under reflux in dry toluene (5 ml) for five hours. The solvent was evaporated and the product chromatographed to yield the title compound (10) (9.8 mg, 25%), $\nu_{max}$ (CHCl$_3$) 1790, 1705 cm$^{-1}$. δppm (CDCl$_3$) 2.57 (2H, d, J 9 Hz; C4—C$\underline{H}_2$) 2.76 (1H, dd, J 17 Hz, 3 Hz, C6—$\underline{H}$, trans), 3.34 (1H, dd, J 17 Hz, 5 Hz, C6—$\underline{H}$, cis), 3.82 (3H, s, CO$_2$C$\underline{H}_3$), 4.00 (1H, m, C5—H), 7.35 (5H, m, Ph), $\lambda_{max}$ (EtOH) 313 nm (ε=11,400). (Found: M, 275.0616, C$_{14}$H$_{13}$NO$_3$S requires 275.0616).

EXAMPLE 4

Benzyl 7-oxo-3-phenylthio-1-azabicyclo[3.2.0]hept-2-ene-2-carboxylate (a) Preparation of 1-(1'-Benzyloxycarbonyl-1'-triphenylphosphoranylidenemethyl)-4-carboxymethylazetidin-2-one

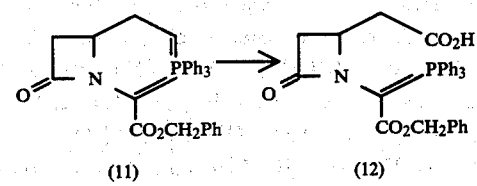

The phosphorane (11, prepared as in Description 3) (2.076 g) in dry methylene chloride (120 ml) was treated with trifluoroacetic acid (3.08 ml). The solution, cooled to −70° C., was ozonised until it became blue. After passing argon through to remove excess ozone, m-chloroperbenzoic (0.69 g) in methylene chloride (25 ml) was added. The stirred mixture was allowed to reach room temperature. After stirring for 3 days, work up and chromatography as in Example 1, gave the phosphorane acid (12) partially as the trifluoroacetic acid salt, as a yellow foam (1.215 g), $\nu_{max}$ (CHCl$_3$) 1770 (shoulder) 1750, 1730, 1700, 1665, 1590, 1575 cm$^{-1}$.

This foam was taken up in chloroform (20 ml) and stirred with basic alumina (4 g) for 4 hours. Evaporation of the filtered solution gave the zwitterionic form of the acid-phosphorane (12) as a foam (0.855 g) $\nu_{max}$(CDCl$_3$) 1735, 1590, 1585, 1575 cm$^{-1}$.

(b) Preparation of 1(1'-benzyloxycarbonyl-1'-triphenylphosphoranylidenemethyl)-4-(phenylthiocarbonylmethyl)azetidine-2-one.

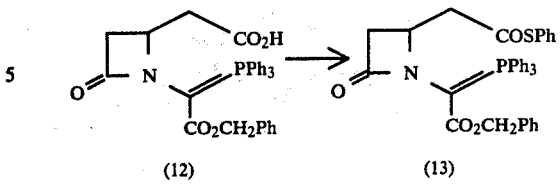

The acid (12) (1.07 g; 2 mmol) and Et$_3$N (220 mg; 2.2 mmol) in dry THF (30 ml) were stirred at RT and a solution of diethyl phosphorochloridate (380 mg; 2.2 mmol) in THF (5 ml) was added dropwise under argon and stirred for three hours at RT. To the solution was added thallium (I) phenylthiolate (686 mg; 2.2 Mmol) and the mixture stirred overnight. The solution was filtered and the solvent evaporated to yield an oil. Chromatography on Merck Kieselgel 60 using ethyl acetate/petrol by gradient elution gave the title product (13), which crystallised from ethyl acetate/ether as a microcrystalline solid mp 160°-1° C., $\nu_{max}$ 1745, 1705, 1620 cm$^{-1}$ (Found: C, 72.12; H, 5.28,; N, 2.15. C$_{38}$H$_{32}$NO$_4$SP requires C, 72.50; H, 5.09; N, 2.23%).

(c) Preparation of benzyl 7-oxo-3-phenylthio-1-azabicyclo[3.2.0]hept-2-ene-2-carboxylate

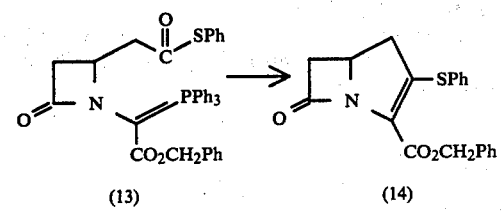

The phosphorane (13) (150 mg) was refluxed in dry toluene (100 ml) under argon for nine hours. The solvent was evaporated and the product chromatographed on Merck Kieselgel 60 using ethyl acetate/petol as eluant to yield the title compound (14) as the major product (25 mg; 30%), $\nu_{max}$ (CHCl$_3$) 1790, 1705 cm$^{-1}$. δppm ((CD$_3$)$_2$CO) 2.72 (2H, s, C4—C$\underline{H}_2$), 2.87 (1H, dd, J 17, 3 Hz, C6—$\underline{H}$, trans), 3.32 (1H, dd, J 17 5½ Hz, C6—H, cis), 4.05 (1H, m, C5—$\underline{H}$), 5.23 (2H, s, CO$_2$C$\underline{H}_2$Ph), 7.20-7.70 (10H, m, SPh and CO$_2$CH$_2$Ph), $\nu_{max}$ (EtOH) 317 nm (ε=12,250). (Found: M, 351.0929, C$_{20}$H$_{17}$NO$_3$S requires 351.0929).

EXAMPLE 5 p-Nitrobenzyl 7-oxo-3-phenylthio-1-azabicyclo[3.2.0]hept-2-ene-2-carboxylate (a) Preparation of 1-(1'-p-Nitrobenzy)oxycarbonyl-1'-triphenylphosphoranylidenemethyl)-4-carboxymethylazetidin-2-one

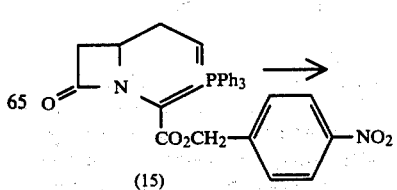

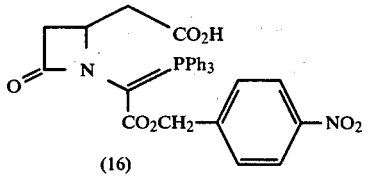

(16)

The phosphorane (15, prepared as in Description 4) (2.82 g) in dry methylene chloride (125 ml) was treated with trifluoroacetic acid (4 ml) at 0°. The solution was cooled to −70° and treated with ozone until blue. Argon was passed through to remove excess ozone, and m-chloroperbenzoic acid (0.9 g) in methylene chloride (20 ml) was added, and the mixture was stirred at RT overnight. The solvent was evaporated, and the resulting white solid was dissolved in ethyl acetate and chromatographed on silica gel. Elution with 10% ethanol-/ethyl acetate gave the product as the trifluoroacetic acid salt. The product was stirred in ethyl acetate with basic alumina (6 g) for two hours. Evaporation of the solvent and trituration of the residue with diethyl ether gave the acid (16) as a light yellow hygroscopic solid (2 g; 69%) solid. A small portion crystallised from diethyl ether gave a microcrystalline solid m.p. 127°–33° C. $\nu_{max}$ (CHCl$_3$) 1745, 1600, 1355, 1115 cm$^{-1}$. (Found: C, 64.59; H, 4.82; N, 4.66. C$_{32}$H$_{27}$N$_2$O$_7$P. ½H$_2$O requires C, 64.97; H, 4.73; N, 4.73).

(b) Preparation of 1-(1'-p-nitrobenzyloxycarbonyl-1'-triphenylphosphoranylidenemethyl)-4-(phenylthiocarbonyl)azetidine-2-one

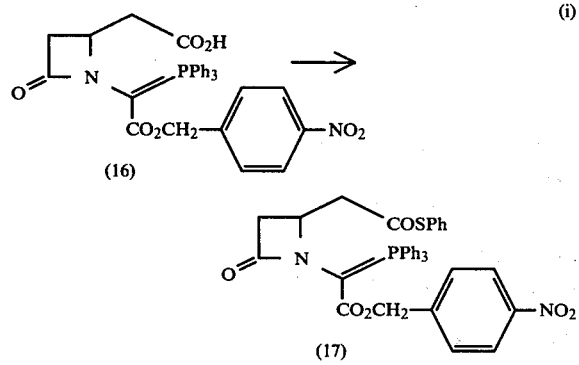

The acid (16) (1.16 g) and Et$_3$N (220 mg) in dry THF (30 ml) were stirred at RT, and a solution of diethyl phosphorochloridate (380 mg) in THF (5 ml) was added dropwise under argon and stirred at RT for three hours. To the solution was added thallium (I) phenylthiolate (686 mg), and the mixture was stirred overnight. The solution was filtered, and the solvent was evaporated. Chromatography yielded the phosphorane thioester (17) as a light tan solid from diethyl ether/ethyl acetate (950 mg; 70%). Recrystallisation from ethyl acetate gave a white solid m.p. 186°–8° C. $\nu_{max}$ (CHCl$_3$) 1745, 1705, 1615, 1350, 1145 cm$^{-1}$. (Found: C, 67.40; H, 4.68; N, 4.02. C$_{38}$H$_{31}$N$_2$O$_6$PS requires C, 67.66; H, 4.60; N, 4.15%).

(ii) Alternative Procedure

The acid, (16, prepared as in (a) above) (2.90 g) and Et$_3$N (550 mg) in dry THF (75 ml) were stirred at RT and a solution of diethyl phosphorochloridate (950 mg) in THF (10 ml) was added dropwise under argon and stirred for three hours at RT. Thiophenol (550 mg) was added to the solution followed by Et$_3$N (550 mg) and the mixture stirred at RT. for two hours. The solvent was evaporated and the residue chromatographed to yield the thioester-phosphorane as a light tan solid from ethyl acetate/ether. Recrystallisation from ethyl acetate gave a white solid, shown by m.p., i.r. and analysis to be identical with (17) as in b (i) above.

(c) Preparation of p-nitrobenzyl 7-oxo-3-phenylthio-1-azabicyclo[3.2.0]hept-2-ene-2-carboxylate

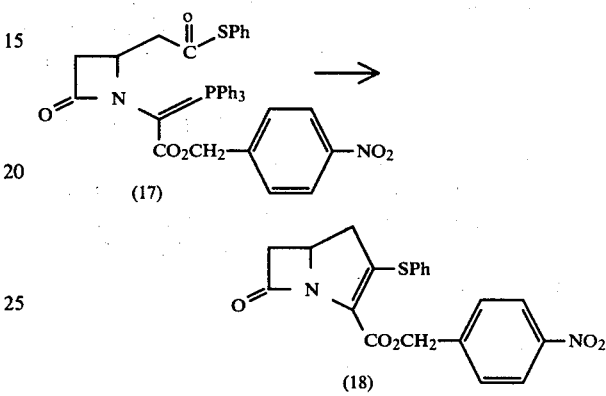

The phosphorane (17) (550 mg) was refluxed in dry toluene (500 ml) for 24 hours with removal of water (Dean-Stark) under argon. The solvent was evaporated and the product chromatographed on florisil (200–300 U.S. mesh) using ethyl acetate/petrol (60°–80°) as eluant to yield the title compound (52 mg: 18%) as a crystalline solid from benzene/petrol (60°–80° C.) mp 112°–4° C. $\nu_{max}$ (CHCl$_3$) 1790, 1705 cm$^{-1}$. δ ppm (CDCl$_3$) 2.63 (2H, d, J 9 Hz, C4—C$_2$), 2.81 (1H, dd, J17, 3 Hz, C6—H trans), 3.38 (1H, dd, J17, 5½ Hz, C6—H, cis), 4.04 (1H, m, C5—H), 5.26 and 5.49 (2H, ABq J14 Hz, benzylic CH$_2$), 7.36 (5H, m, SPh), 7.60 (d, 2H, J9 Hz, PhNO$_2$), 8.15 (d, 2H, J9 Hz, PhNO$_2$) $\lambda_{max}$ (EtOH) 266 nm (ε10,200), 317 nm (ε8,900) (Found: C, 60.56; H, 3.93; N, 6.91% C$_{20}$H$_{16}$N$_2$O$_5$S requires C, 60.61; H, 4.04; N, 7.07%).

EXAMPLE 6

Benzyl 7-oxo-3-p-acetamidophenylthio-1-azabicyclo[3.2.0-]hept-2-ene-2-carboxylate (a) Preparation of 4-(p-Acetamidophenylthiocarbonylmethyl)-1(1'-benzyloxycarbonyl-1'-triphenylphosphoranylidenemethyl)azetidin-2-one

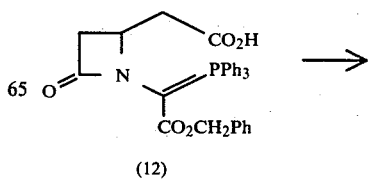

(12)

-continued

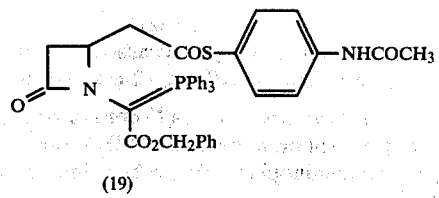

(19)

The acid (12; prepared as in Example 4a) (268 mg) in dry tetrahydrofuran (10 ml) under argon was treated with triethylamine (76 mg), followed by diethylphosphorochloridate (130 mg), diluted with tetrahydrofuran (5 ml). After stirring at room temperature for 3 hours, the solution was added to freshly prepared sodium p-acetamidophenylthiolate in tetrahydrofuran [prepared by treating p-acetamidophenylthiol (92 mg) in dry tetrahydrofuran (5 ml)/hexamethylphosphoramide (89 mg), under argon, at 0°, with sodium hydride (26 mg of a 50% suspension in oil)].

The stirred mixture was allowed to warm up from 0° to room temperature over 30 minutes, and after a further hour was diluted with ethyl acetate (60 ml), washed with water, then brine, dried over magnesium sulphate and filtered and the filtrate was evaporated. Chromatography on Merck Kieselgel 60 (10 g), eluting with ethyl acetate, gave the required thioester (19) as white crystals (128 mg). Recrystallisation from chloroform/ethyl acetate gave white needles m.p. 181°–3° C., $\nu_{max}$ (Nujol) 1730, 1700, (broad), 1620, 1590 cm$^{-1}$. $\nu_{max}$ (KBr) 1730, 1695 (broad), 1620, 1595 cm$^{-1}$. (Found: C, 69.81; H, 5.32; N, 4.35. $C_{40}H_{35}N_2SO_5P$ requires C, 70.00; H, 5.10; N, 4.08%).

Note: This thioester (19) was also prepared substituting the sodium thiolate mixture by solid thallium (I) p-acetamidophenylthiolate. A comparable yield was obtained.

(b) Preparation of Benzyl 7-oxo-3-p-acetamidophenylthio-1-azabicyclo[3.2.0]hept-2-ene-2-carboxylate

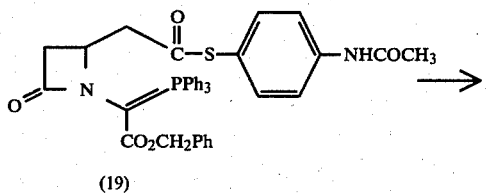

(19)

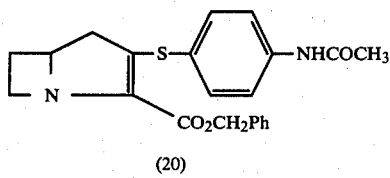

(20)

The phosphorane (19) (136 mg) was suspended in dry toluene (10 ml) and the mixture was evaporated to dryness. The residue was suspended in dry toluene (60 ml), and the mixture was degassed and heated, under argon, under reflux with a Dean-Stark head. After 5 hours the pale yellow solution was cooled to room temperature, and the solvent was evaporated. The residue was taken up in ethyl acetate (12 ml), and left overnight at 5°, when buff coloured crystals were obtained. These were collected (97.5 mg) and shown by thin layer chromatography to be recovered starting material. The solution was evaporated, and the residue was chromatographed on Merck Keiselgel 60, eluting with ethyl acetate/petrol mixtures to give the required compound (20), initially as a gum (7.5 mg) contaminated with triphenylphosphine oxide. Trituration of this gum with diethyl ether gave (20), as a white solid (4.2 mg), $\nu_{max}$ (CHCl$_3$) 1782, 1700 (shoulder), 1695, 1590 cm$^{-1}$. $\nu_{max}$ (ethanol) 312 nm and 245 nm. δppm (CDCl$_3$) 2.12 (s, 3H, C$\underline{H}_3$); 2.57 (2H, d, J 8 Hz, C4—C$\underline{H}_2$), 2.74 (1H, dd, J 16 Hz, 3 Hz, C6—$\underline{H}$); 3.32 (1H, dd, J 16 Hz, 5 Hz, C6—$\underline{H}$); 4.00 (1H, m, C5—$\underline{H}$); 5.27 (2H, s, C$\underline{H}_2$Ph); 7.12–7.62 (14H, Ar+Ph$_3$P=O); 7.71 (1H, s, N$\underline{H}$).

EXAMPLE 7

Benzyl 7-oxo-3-p-aminophenythio-1-azabicyclo[3.2.0]hept-2-ene-2-carboxylate (a) Preparation of 4-(p-Aminophenylthiocarbonylmethyl)-1(1'-benzyloxycarbonyl-1'-triphenylphosphoranylidenemethyl)azetidin-2-one

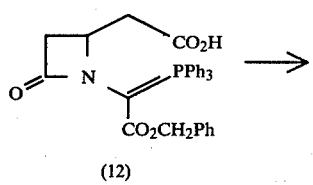

(12)

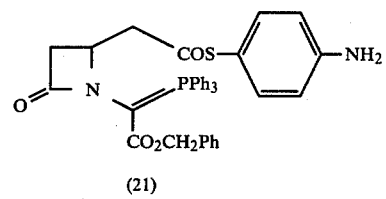

(21)

The acid (12, prepared as in Example 4a), (1.675 g) in dry tetrahydrofuran (80 ml), under argon, was treated with triethylamine (0.472 g) and diethylphosphorochloridate (0.807 g). After stirring at room temperature for 3 hours the reaction mixture was added to freshly prepared sodium p-amino-phenylthiolate in tetrahydrofuran [prepared by treating p-aminophenylthiol (0.428 g) in dry tetrahydrofuran (30 ml)/hexamethylphosphoramide (0.505 g), under argon at 0°, with sodium hydride (0.165 g of a 50% suspension in oil)].

The stirred mixture was allowed to warm from 0° to room temperature. After a total of 1.5 hours, work-up as in Example 6, followed by chromatography on Merck Keisel gel 60 (60 g), eluting with from 50% ethyl acetate gave the required thioester (21) as a cream coloured solid (0.9 g). Recrystallisation of a portion from hot ethyl acetate/petroleum ether (60°–80°) gave "spherical crystals" m.p. 114.5°–118°, $\nu_{max}$ (CHCl$_3$) 3330, 1738, 1685 (broad, weak), 1620, 1600 (shoulder)cm$^{-1}$.

(b) Preparation of Benzyl 7-oxo-3-p-aminophenylthio-1-azabicyclo[3.2.0]hept-2-ene-2-carboxylate

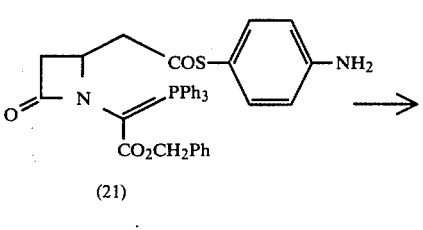

(21)

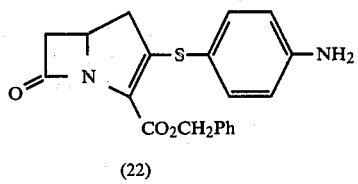

(22)

The phosphorane (21) (0.461 g) was taken up in dry toluene, and the mixture was evaporated to dryness. The residue was suspended in dry toluene (250 ml), and the mixture was degassed and heated to reflux. A pale yellow solution was obtained. After refluxing for 6.5 hours the solution was left in the refrigerator overnight. The toluene solution was decanted from some gummy material and evaporated to dryness. Trituration of the residue with dry diethyl ether gave recovered (21) as a solid (414 mg). The ethereal solution was evaporated to dryness and the residue was taken up in toluene and chromatographed on Merck Keiselgel 60 (4 g), eluting with mixtures of ethyl acetate and petroleum ether (60°–80° C.), to give the required bicyclic product (22) as a gum (3.5 mg). $\nu_{max}$ (CHCl$_3$) 3300 (weak), 1780 (strong), 1700, 1685, (weak), 1620, 1600 cm$^{-1}$. $\lambda_{max}$ (ethanol) at 314 nm and 261.5 nm.

(Treatment of this p-aminophenylthio compound (22) with triethylamine;/acetyl chloride gave the p-acetamidophenylthio compound (20) as shown by thin layer chromatography).

Example 8

Preparation of Benzyl 7-oxo-3-p-aminophenylthio-1-azabicyclo[3.2.0]hept-2-ene-2-carboxylate (Alternative Procedure)

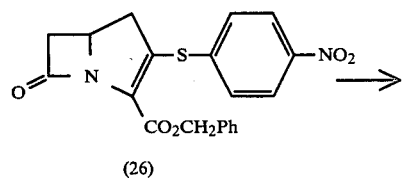

(26)

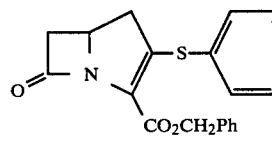

(22)

A catalyst of 10% palladium on charcoal (Engelhard 4505, 50 mg) suspended in 90% aqueous ethanol (10 ml) was prehydrogenated for 20 minutes at room temperature/atmospheric pressure. Benzyl 7-oxo-3-p-nitrophenylthio-1-azabicyclo [3.2.0]hept-2-ene-2-carboxylate (50 mg) partially dissolved in ethanol (10 ml) was added, and the mixture was hydrogenated at room temperature and atmospheric pressure for 1.5 hours. The catalyst was removed by filtration through "High-Flo", and the colourless filtrate was evaporated to give an oil (35 mg) identical by TLC, u.v. and I.R. to the product (22) obtained in Example 7.

EXAMPLE 9

Benzyl 7-oxo-3-(4-p-nitrobenzyloxycarbonylaminophenylthio)-1-azabicyclo[3.2.0]hept-2-ene-2-carboxylate (a) Preparation of 1-(1′-Benzyloxycarbonyl-1-triphenylphosphoranylidenemethyl)-4-(p-nitrobenzyloxycarbonylaminophenylthiocarbonylmethyl)azetidin-2-one

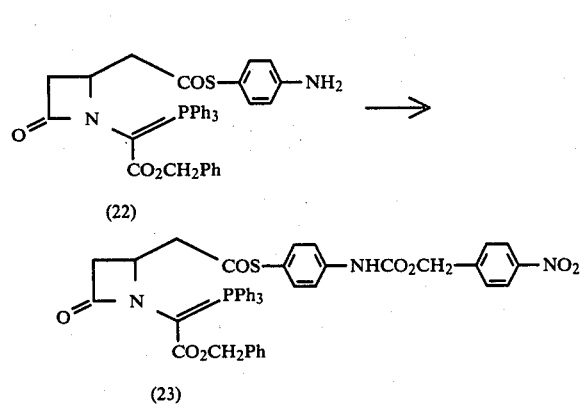

The phosphorane (22) (438 mg) in dry tetrahydrofuran (60 ml), under argon was treated with powdered sodium hydroxide (27.2 mg) and p-nitrobenzylchloroformate (147 mg). After stirring at room temperature for 1.5 hours, the solvent was removed by evaporation, and the residue was taken up in chloroform, washed with brine, dried over magnesium sulphate and filtered, and the filtrate was evaporated. Chromatography on Merck Keiselg el 60, eluting with from 50% ethyl acetate in petroleum ether (60°–80°) to neat ethyl acetate gave the required thioester (23) as a white solid (255 mg), contaminated with a little starting material (22). Further elution with a mixture of chloroform/ethyl acetate gave a further (109 mg) of the required product (23). A portion was recrystallised from chloroform/ether. The crystals were dried in vacuo at 100° C. for a total of 11 hours, to give the fine white crystals m.p. 205°–7° C. (dec.) $\nu_{max}$ (nujol) 1742, 1738, 1700, 1680 (weak), 1605, 1590, 1518, 1345 cm$^{-1}$. Found: C, 65.52; H, 4.46; N, 4.86. C$_{46}$H$_{38}$N$_3$O$_8$SP.H$_2$O requires: C, 65.50; H, 4.75; N, 4.98%).

(b) Preparation of Benzyl 7-oxo-3-(4-p-nitrobenzyloxycarbonylaminophenylthio)-1-azabicyclo[3.2.0] hept-2-ene-2-carboxylate

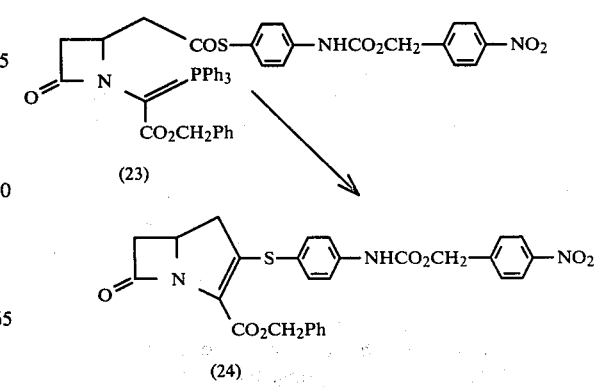

The phosphorane (23) (850 mg) was suspended in dry toluene (500 ml) and heated under an atmosphere of argon under reflux using a Dean-Stark apparatus to remove water. A clear, pale yellow solution was obtained. After refluxing for 6.5 hours the slightly darker solution was cooled and reduced by evaporation to about 150 ml. On storing overnight at 5°, recovered starting material (551 mg) was precipitated. The solution was evaporated, and the residue was chromatographed on florisil (200–300 U.S. mesh). Elution with 20–30% ethyl acetate in petroleum ether (60°–80° C.) gave the required bicyclic compound (24) contaminated with triphenylphosphine oxide and some nonbicyclic β-lactam containing material as a gum (37.5 mg). Trituration of this gum with diethyl ether gave a white solid (14.8 mg). This solid was recrystallised from ethyl acetate/petroleum ether (60°–80° C.) to give the bicyclic compound (24) as fine white crystals m.p. 130°–8° C., $\nu_{max}$ (CHCl$_3$) 1780 (strong) 1738, 1700, 1685, 1510, 1345 cm$^{-1}$. $\lambda_{max}$ (ethanol) 251 nm ($\epsilon$=23,700) and 316 nm ($\epsilon$=16,700). δppm (CDCl$_3$) 2.56 (2H, d, J 9 Hz, C4—H's), 2.74 (1H, dd, J 16 Hz, 2.5 Hz, C6—H); 3.35 (1H, dd, J 16 Hz, 5 Hz, C6—H); 3.85 (1H, centre of m, C5—H); 5.24 (2H, s, CH$_2$Ar); B 5.26 (2H, s, CH$_2$Ar); 6.76 (1H, s, NH); 7.15-7.55 (11H, Ar); 8.0-8.25 (2H, Ar).

EXAMPLE 10

Benzyl 3-p-nitrophenylthio-7-oxo-1-azabicyclo[3.2.0]hept-2-ene-2-carboxylate (a) Preparation of 1-(1'-Benzyloxycarbonyl-1'-triphenylphosphoranylidenemethyl)-4-(n-nitrophenylthiocarbonylmethyl)azetidin-2-one

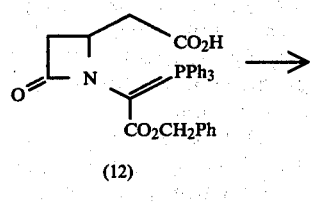

(12)

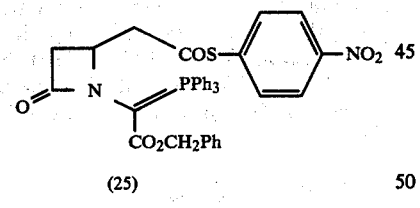

(25)

The acid (12, prepared as in Example 4a), (4.39 g) in dry tetrahydrofuran (150 ml), under argon, was treated with triethylamine (1.78 ml) and diethylphosphorochloridate (2.13 g). After stirring at room temperature for 3 hours, the reaction mixture was added to freshly prepared sodium p-nitrophenylthiolate in tetrahydrofuran at 0° [prepared by treating dried p-nitrophenylthio (1.4 g) in dry tetrahydrofuran (75 ml), under argon at 0° with sodium hydride (0.426 g of a 50% suspension in oil)].

The stirred red mixture was kept below 10° (internal temperature) for 1.5 hours. After reducing the volume by evaporation, ethyl acetate (500 ml) was added, and the reaction mixture was washed with brine, dried over magnesium sulphate and filtered, and the filtrate was evaporated. Chromatography of the residue on silica 60 (<230 mesh) (80 g), eluting with ethyl acetate gave the required thioester (25) (2.6 g). Crystallisation from ethyl acetate/ether gave yellow crystals m.p. 169°–70° C. $\nu_{max}$ (CHCl$_3$) 1745, 1720 (sh), 1630 cm$^{-1}$. (Found: C, 67.53; H, 4.57; N, 3.93%. C$_{38}$H$_{31}$N$_2$O$_6$SP requires C, 67.66; H, 4.60; N, 4.15%.

(b) Preparation of Benzyl 3-p-nitrophenylthio-7-oxo-1-azabicyclo[3.2.0]hept-2-ene-2-carboxylate

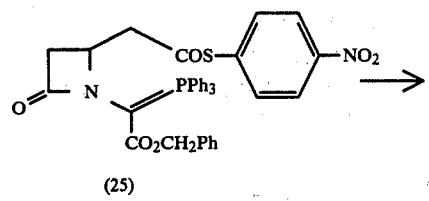

(25)

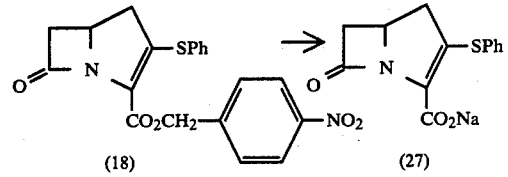

(26)

The phosphorane (25) (1.0 g) in dry toluene (600 ml) was heated under an atmosphere on argon under reflux using a Dean-Stark apparatus to remove water. After 1.5 hours the dark solution was rapidly cooled, evaporated almost to dryness, then chromatographed on 30 g silica 60 (230–400 mesh). Elution with 30% ethyl acetate in petroleum ether (60°–80° C.) gave the required product (26), (41 mg) as yellow crystals from ethyl acetate m.p. 126°–31°.

(CHCl$_3$) 1795, 1710, 1525, 1345 cm$^{-1}$. δppm [(CD$_3$)$_2$CO] 3.00 (2H, d, J 10 Hz, C4—CH$_2$), 3.07 (1H, dd, J 17, 4 Hz, C6—H trans), 3.52 (1H, dd, J 17, 6 Hz, C6-H cis), 4.21 (1H, m, C5—H), 5.36 (2H, s, CH$_2$), 7.47 (5H, m, Ph), 7.92 and 8.32 (4H, ABq, J 9 Hz, SPhNO$_2$). $\lambda_{max}$(EtOH) 261 nm ($\epsilon$=8,430), 312 nm ($\epsilon$=10,219) 343 nm (sh) ($\epsilon$=8,500).

EXAMPLE 11

Sodium 7-oxo-3-phenylthio-1-azabicyclo-[3.2.0]hept-2-ene-2-carboxylate

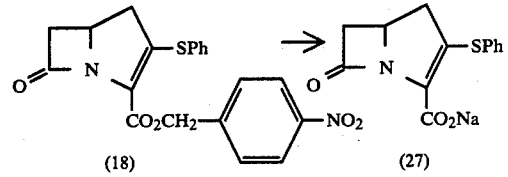

(18) (27)

The p-nitrobenzyl ester (18) (70 mg) was dissolved in 30% aqueous dioxan containing 5% Pd/C (90 mg) [prehydrogenated for twenty minutes]. The solution was hydrogenated at ambient temperature and pressure for one hour. Examination of the solution by u.v. showed a shift of chromophoric absorption of 316 nm and 266 nm for the p-nitrobenzyl ester to 314 nm and 251 nm respectively for the product. The soltuion was treated with one equivalent of NaHCO$_3$ (14.7 mg) in water (2 ml) and filtered through keiselguhr. The organic solvent was removed under reduced pressure until cloudiness occurred and extracted with ethyl acetate (3×10 ml). The water was evaporated to low volume (approx. 2 ml) and loaded onto a biogel P2 column. Elution with water and collection of 10 ml fractions gave the sodium salt in fractions 11 and 12. The solvent was evaporated under high vacuum, and the solid obtained by evaporation of solvent twice from ethanol (2×10 ml) and twice from toluene (2×15 ml) to yield (27) as a light yellow solid (12 mg). $\nu_{max}$ (KBr disc) 1755 cm$^{-1}$, $\nu_{max}$ (EtOH) 302 nm.

EXAMPLE 12

Phthalidyl 7-oxo-3-phenylthio-1-azabicyclo-[3,2,0]hept-2-ene-2-carboxylate

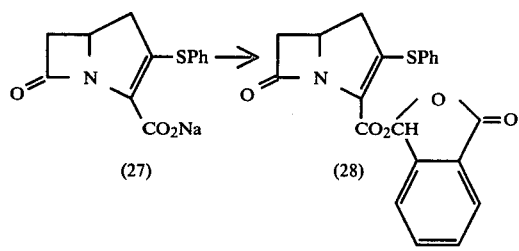

The sodium salt (14 mg) was dissolved in DMF (2 ml) and treated with bromophthalide (10 mg). The solution was stirred at RT for 3 hours, the solvent was evaporated, and the residue was dissolved in ethyl acetate and washed with brine (2×5 ml). The organic phase was dried (MgSO$_4$) and evaporated to yield an oil which after chromatography gave (28) as an oil (3 mg) $\nu_{max}$ (CHCl$_3$) 1795, 1730 cm$^{-1}$. δppm (CDCl$_3$) 2.69 (2H, d, J9.5 Hz, C4—C$\underline{H_2}$), 2.81 (1H, dd, J 16.5, 3.5 Hz, C6—$\underline{H}$a), 3.38 (1H, dd, J16.5 5.5 Hz, C6—$\underline{H}$b) 4.07 (1H, m, C5-$\underline{H}$) 6.55 (½H, s, CO$_2$C$\underline{H}$ from one isomer) 7.20 to 8.00 (9½H, m, aromatics plus CO$_2$C$\underline{H}$ from the second isomer) λ$_{max}$ 322 nm.

EXAMPLE 13

Pivaloyloxymethyl 7-oxo-3-phenylthio-1-azabicyclo [3.2.0] hept-2-ene-2-carboxylate Preparation of 1-(1'-pivaloyloxycarbonyl)-1'-triphenylphosphoranylidenemethyl)-4-carboxymethylazetidin-2-one

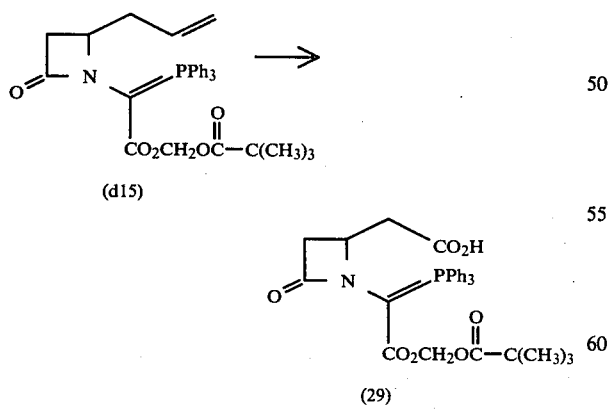

The phosphorane (d15, prepared as in Description 5) (258 mg) was dissolved in dry methylene choride (15 ml) containing trifluoroacetic acid (0.8 ml) and stirred at RT. for ten minutes. The solution was cooled to −70° and ozonised for 15 minutes until a blue colour persisted. Argon was passed through the solution to remove excess ozone and m-chloroperbenzoic acid (90 mg) in methylene chloride (5 ml) was added. The mixture was allowed to warm up to RT. and stirred overnight. The solvent was evaporated and the residue chromatographed (Kieselgel 60, <230 mesh) to yield the phosphorane acid (29) as the trifluoroacetic acid salt. The salt was dissolved in methylene chloride and stirred with basic alumina (500 mg) for one hour. The solution was filtered and evaporated to yield the phosphorane-acid (29) as a colourless foam (198 mg) $\nu_{max}$ (CHCl$_3$) 1730, 1600 cm$^{-1}$.

(b) Preparation of 1-(1'-pivaloyloxymethyloxycarbonyl-1'-triphenylphosphoranylidenemethyl)-4-(phenylthiocarbonylmethyl)azetidin-2-one.

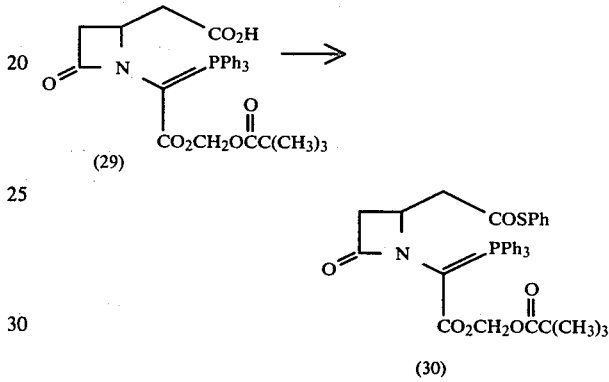

The acid (29) (187 mg) was dissolved in dry THF containing Et$_3$N (34 mg) and a solution of diethylphosphorochloridate (61 mg) in dry THF (2 ml) was added dropwise under argon. The reaction was stirred at RT. for three hours and thallium (I) phenylthiolate (105 mg) was added. The reaction was stirred overnight, filtered and the solvent evaporated. The resulting oil was chromatographed on Merck Kieselgel 60 (<230 mesh) using ethyl acetate/petrol (60–80) as eluant to yield the title compound (30) as a colourless oil which crystallised from ether as a white solid m.p. 149°-50° (120 mg; 55%). $\nu_{max}$ (CHCl$_3$) 1735, 1700 (sh), 1630 cm$^{-1}$.

(c) Preparation of pivaloyloxymethyl 7-oxo-3-phenylthio-1-azabicyclo[3.2.0]hept-2-ene-2-carboxylate

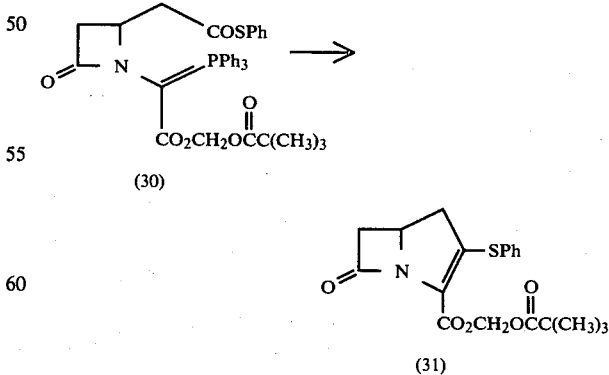

The phosphorane (30) (218 mg) was refluxed in dry toluene (250 ml) under argon for 18 hours. The solvent was evaporated and the residue chromatographed on florisil (200–300 U.S. mesh) using slight pressure and ethyl acetate/petrol (60–80) as eluant. The title compound (31) was collected as a colourless oil (6 mg; 5%) $\nu_{max}$ (CHCl$_3$) 1780, 1750, 1725 cm$^{-1}$. δppm (CDCl$_3$), 1.22 (9H, s, C(C$\underline{H}_3$)$_3$) 2.62 (2H, d, J 9.5 Hz, C4—C$\underline{H}_2$) 2.78 (1H, dd, J 16 Hz, 3 Hz, C6—$\underline{H}$, trans), 3.36 (1H, dd, J 16 Hz, 5 Hz, C6—$\underline{H}$, cis) 4.00 (1H, m, C5—$\underline{H}$) 5.87 and 5.98 (2H, ABq, J 5.5 Hz, OC$\underline{H}_2$O) 7.40 (5H, m, Ph), $\lambda_{max}$ (EtOH) 319 nm.

| | PHARMACOLOGICAL DATA In Vitro Antibacterial Testing Concentration of Compounds showing growth inhibition μg/ml | | | | | | | | |
|---|---|---|---|---|---|---|---|---|---|
| Dilution in DST agar + 5% Horse blood | Inoculum 10$^{-4}$ dilution COMPOUND | | | | | | | | |
| ORGANISM | 10 | 14 | 18 | 20 | 22 | 24 | 26 | 27 | 28 |
| *Bacillus subtilis* A | <2 | 20 | 20 | 20 | 25 | ≦2 | 10 | 1.9 | 5.5 |
| *E.coli* 0111 | >100 | 20 | 200 | 20 | >100 | 200 | >50 | 5.5 | 16.6 |
| *Klebsiella aerogenes* A | 20 | 200 | 20 | 200 | >100 | >200 | >50 | 5.5 | 5.5 |
| *Proteus mirabilis* C977 | >100 | 20 | 200 | 200 | >100 | >200 | >50 | 16.6 | 50 |
| *Salmonella typhimurium* CT10 | >100 | 20 | 200 | 200 | >100 | >200 | >50 | 16.6 | 50 |
| *Serratia marcescens* US20 | >100 | 20 | >200 | >200 | >100 | >200 | >50 | >50 | >50 |
| *Shigella sonnei* MB 11967 | >100 | 20 | 200 | 200 | >100 | >200 | >50 | 5.5 | 16.6 |
| *Staph.aureus* Oxford | >100 | 20 | 200 | 200 | 100 | ≦2 | >50 | 50 | 16.6 |
| *Staph.aureus* Russell | 20 | 20 | 200 | 200 | >100 | 20 | 50 | 16.6 | 50 |
| *Strep.pneumoniae* | 20 | 20 | 2 | 20 | 10 | ≦2 | 10 | — | — |
| *Strep.pyogenes* CN10 | 20 | 20 | 2 | 20 | 5 | ≦2 | 10 | 5.5 | 5.5 |

Note:
Compound (10) tested at 100, 20 and 2 μg/ml
Compounds (14), (18) and (20) tested at 200, 20 and 2 μg/ml
Compound (22) tested by twofold serial dilution
Compound (26) tested at 50, 10 and 1 μg/ml
Compounds (27) and (28) tested by 1 in 3 serial dilutions

What we claim is:

1. A compound of the formula (II):

(II)

wherein $R_1$ is a group such that $CO_2R_1$ is a carboxylic acid group or a pharmaceutically acceptable salt or a lower alkyl ester, a lower alkoxyl lower alkyl ester, the benzyl ester, a lower alkoxy benzyl ester, a nitrobenzyl ester, a chlorobenzyl ester or an in-vivo hydrolyzable ester thereof selected from the group consisting of the acetoxymethyl, pivaloyloxymethyl, α-ethoxycarbonyloxyethyl and phthalidyl esters and $R_2$ is phenyl or phenyl substituted by one to four substituents selected from the group consisting of lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$, and $CO_2R_{10}$ wherein $R_3$ is lower alkyl, benzyl, fluorobenzyl, chlorobenzyl, bromobenzyl or nitrobenzyl and $CO_2R_{10}$ is carboxyl or a pharmaceutically acceptable salt thereof, not more than three such substituents being selected from the group consisting of fluorine, chlorine, bromine, CN, $NO_2$, $NH_2$, $COR_3$ and $CO_2R_3$ and not more than two such substituents being selected from the group consisting of CN, $NO_2$ and $NH_2$.

2. A compound according to claim 1 wherein $R_2$ is phenyl group or phenyl substituted by one or two substituents selected from the group consisting of fluorine, chlorine, bromine, CN, $NO_2$, $COR_3$, $OR_3$, $NHCOR_3$, $NHCO_2R_3$ and $CO_2R_3$ wherein $R_3$ is lower alkyl or benzyl.

3. A compound according to claim 2 wherein $R_1$ is a group such that $CO_2R_1$ is a lower alkyl ester, a lower alkoxyl lower alkyl ester, the benzyl ester, a lower alkoxyl benzyl ester, a nitrobenzyl ester, a chlorobenzyl ester or an in-vivo hydrolyzable ester.

4. A compound according to claim 1 wherein $R_2$ is phenyl, p-nitrophenyl, p-aminophenyl, p-acetamidophenyl or p-(4'-nitrobenzyloxycarbonylamino)phenyl.

5. A compound according to claim 1 wherein $R_1$ is phthalidyl.

6. A compound according to claim 1 wherein $R_1$ is p-nitrobenzyl.

7. A compound according to claim 1, wherein $R_1$ is a group such that the compound is a carboxylic acid salt.

8. A compound according to claim 7 wherein $R_1$ is sodium or potassium.

9. A compound according to claim 1 which is t-butyl 7-oxo-3-p-nitrophenylthio-1-azabicyclo[3.2.0]hept-2-ene-2-carboxylate, t-butyl 7-oxo-3-phenylthio-1-azabicyclo[3.2.0]hept-2-ene-2-carboxylate, methyl 7-oxo-3-phenylthio-1-azabicyclo[3.2.0]hept-2-ene-2-carboxylate, benzyl 7-oxo-3-phenylthio-1-azabicyclo[3.2.0]hept-2-ene-2-carboxylate, p-nitrobenzyl 7-oxo-3-phenylthio-1-azabicyclo[3.2.0]hept-2-ene-2-carboxylate, benzyl 7-oxo-3-p-acetamidophenylthio-1-azabicyclo[3.2.0]hept-2-ene-2-carboxylate, benzyl 7-oxo-3-p-aminophenylthio-1-azabicyclo[3.2.0]hept-2-ene-2-carboxylate, benzyl 7-oxo-3-p-(4'-nitrobenzyloxycarbonylamino)phenylthio-1-azabicyclo[3.2.0]hept-2-ene-2-carboxylate, benzyl 7-oxo-3-p-nitrophenylthio-1-azabicyclo[3.2.0]hept-2-ene-2-carboxylate, sodium 7-oxo-3-phenylthio-1-azabicyclo[3.2.0]hept-2-ene-2-carboxylate, phthalidyl 7-oxo-3-phenylthio-1-azabicyclo[3.2.0-]hept-2-ene-carboxylate or pivaloyloxymethyl 7-oxo-3-phenyl-1-azabicyclo[3.2.0]hept-2-ene-2-carboxylate.

10. A compound according to claim 4 wherein $R_1$ is phthalidyl.

11. A compound according to claim 4 wherein $R_1$ is p-nitrobenzyl.

12. A compound according to claim 1 wherein $R_2$ is phenyl, p-chlorophenyl, m-chlorophenyl, p-nitrophenyl, m-nitrophenyl, p-ethoxycarbonylphenyl, p-fluorophenyl, p-methylphenyl, p-aminophenyl, p-acetamidophenyl, p-(4'-nitrobenzyloxycarbonylamino)phenyl or p-methoxyphenyl.

13. A compound according to claim 1 having the R-configuration at C-5.

14. A compound according to claim 1 having the S-configuration at C-5.

15. A compound according to claim 1 which is a mixture of isomers having the R- and S- configurations at C-5.

16. A compound according to claim 1 of the formula (IV):

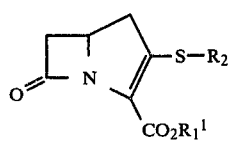

wherein $R_1^1$ is a group such that $CO_2R_1^1$ is an in-vivo hydrolyzable ester and $R_2$ is phenyl or phenyl substituted by one to four substituents selected from the group consisting of lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$ and $CO_2R_{10}$ wherein $R_3$ is lower alkyl, benzyl, fluorobenzyl, chloroenzyl, bromobenzyl or nitrobenzyl and $CO_2R_{10}$ is carboxyl or a pharmaceutically acceptable salt thereof, not more than three such substituents being selected from the group consisting of fluorine, chlorine, bromine, CN, $NO_2$, $NH_2$, $COR_3$ and $CO_2R_3$ and not more than two such substituents being selected from the group consisting of CN, $NO_2$ and $NH_2$.

17. A compound according to claim 16 wherein $R_1^1$ is acetoxymethyl, pivaloyloxymethyl, α-ethoxycarbonyloxyethyl or phthalidyl.

18. A compound according to claim 1 of the formula (VI):

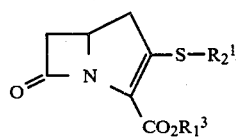

wherein $R_1^3$ is tert-butyl, methyl, benzyl, p-nitrobenzyl, phthalidyl, pivaloyloxymethyl or sodium; and $R_2^1$ is p-acetamidophenyl, p-nitrophenyl, p-aminophenyl or p-(4'-nitrobenzyloxycarbonylamino)phenyl.

19. A compound according to claim 18 wherein $R_1^3$ is p-nitrobenzyl, phthalidyl or sodium.

20. A pharmaceutical composition useful for the treatment or prophylaxis of bacterial infections in humans and animals which comprises an effective amount of a compound of the formula (II):

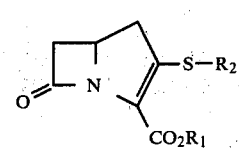

wherein $R_1$ is a group such that $CO_2R_1$ is a carboxylic acid group or a pharmaceutically acceptable salt or a lower alkyl ester, a lower alkoxyl lower alkyl ester, the benzyl ester, a lower alkoxyl benzyl ester, a nitrobenzyl ester, a chlorobenzyl ester or an in-vivo hydrolyzable ester thereof selected from the group consisting of the acetoxymethyl, pivaloyloxymethyl, α-ethoxycarbonyloxyethyl and phthalidyl esters and $R_2$ is phenyl or phenyl substituted by one to four substituents selected from the group consisting of lower alkyl, fluorine, chlorine, bromine, CH, $NO_2$, $COR_3$, $OR_3$, $SR_3$, $NH_2$, $NHCOR_3$, $NHCO_2R_3$, $CO_2R_3$ and $CO_2R_{10}$ wherein $R_3$ is lower alkyl, benzyl, fluorobenzyl, chlorobenzyl, bromobenzyl or nitrobenzyl and $CO_2R_{10}$ is carboxyl or a pharmaceutically acceptable salt thereof, not more than three such constituents being selected from the group consisting of fluorine, bromine, CN, $NO_2$, $NH_2$, $COR_3$ and $CO_2RHD$ 3 and not more than two such substituents being selected from the group consisting of CN, $NO_2$ and $NH_2$, in combination with a pharmaceutically acceptable carrier.

21. A composition according to claim 20 wherein $R_2$ is phenyl group or phenyl substituted by one or two substituents selected from the group consisting of fluorine, chlorine, bromine, CN, $NO_2$, $COR_3$, $OR_3$, $NHCOR_3$, $NHCO_2R_3$ and $CO_2R_3$ wherein $R_3$ is lower alkyl or benzyl.

22. A composition according to claim 21 wherein $R_1$ is a group such that $CO_2R_1$ is a lower alkyl ester, a lower alkoxyl lower alkyl ester, the benzyl ester, a lower alkoxyl benzyl ester, a nitrobenzyl ester, a chlorobenzyl ester or an in-vivo hydrolyzable ester.

23. A composition according to claim 20 wherein $R_2$ is phenyl, p-nitrophenyl, p-aminophenyl, p-acetamidophenyl or p-(4'-nitrobenzyloxycarbonylamino)phenyl.

24. A composition according to claim 20 wherein $R_1$ is phthalidyl.

25. A composition according to claim 20 wherein $R_1$ is p-nitrobenzyl.

26. A composition according to claim 20 wherein $R_1$ is a group such that the compound is a carboxylic acid salt.

27. A composition according to claim 20 wherein $R_1$ is sodium or potassium.

28. A composition according to claim 20 wherein the compound is t-butyl 7-oxo-3-p-nitrophenylthio-1-azabicyclo[3.2.0]hept-2-ene-2-carboxylate, t-butyl 7-oxo-3-phenylthio-1-azabicyclo[3.2.0]hept-2-ene-2-carboxylate, methyl 7-oxo-3-phenylthio-1-azabicyclo[3.2.0]hept-2-ene-2-carboxylate, benzyl 7-oxo-3-phenylthio-1-azabicyclo[3.2.0]hept-2-ene-2-carboxylate, p-nitrobenzyl 7-oxo-3-phenylthio-1-azabicyclo[3.2.0-]hept-2-ene-2-carboxylate, benzyl 7-oxo-3-p-acetamidophenylthio-1-azabicyclo[3.2.0]hept-2-ene-2-carboxylate, benzyl 7-oxo-3-p-aminophenylthio-1-azabicyclo[3.2.0]hept-2-ene-2-carboxylate, benzyl 7-oxo-3-p-(4'-nitrobenzyloxycarbonylamino)-phenylthio-1-azabicyclo[3.2.0]hept-2-ene-2-carboxylate, benzyl 7-oxo-3-p-nitrophenylthio-1-azabicyclo[3.2.0]hept-2-ene-2-carboxylate, sodium 7-oxo-3-phenylthio-1-azabicyclo[3.2.0]hept-2-ene-2-carboxylate, phthalidyl 7-oxo-3-phenylthio-1-azabicyclo[3.2.0]hept-2-ene-2-carboxylate or pivaloyloxymethyl 7-oxo-3-phenyl-1-azabicyclo[3.2.0]hept-2-ene-2-carboxylate.

29. A composition according to claim 23 wherein $R_1$ is phthalidyl.

30. A composition according to claim 23 wherein $R_1$ is p-nitrobenzyl.

31. A composition according to claim 20 wherein $R_2$ is phenyl, p-chlorophenyl, m-chlorophenyl, p-nitrophenyl, m-nitrophenyl, p-ethoxycarbonylphenyl, p-fluorophenyl, p-methylphenyl, p-aminophenyl, p-acetamidophenyl, p-(4'-nitrobenzyloxycarbonylamino)-phenyl or p-methoxyphenyl.

32. A composition according to claim 20 wherein the compound has the R- configuration at C-5.

33. A composition according to claim 20 wherein the compound has the S- configuration at C-5.

34. A composition according to claim 20 wherein the compound is a mixture of isomers having the R- and S-configuration at C-5.

35. A composition according to claim 20 wherein the compound is of the formula (IV):

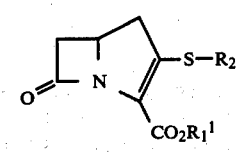

(IV)

wherein $R^1_1$ is a group such that $CO_2R^1_1$ is an in-vivo hydrolyzable ester and $R_2$ is phenyl or phenyl substituted by one to four substituents selected from the group consisting of lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$ and $CO_2R_{10}$ wherein $R_3$ is lower alkyl, benzyl, fluorobenzyl, chlorobenzyl, bromobenzyl or nitrobenzyl and $CO_2R_{10}$ is carboxyl or a pharmaceutically acceptable salt thereof, not more than three such substituents being selected from the group consisting of fluorine, chlorine, bromine, CN, $NO_2$, $NH_2$, $COR_3$ and $CO_2R_3$ and not more than two such substituents being selected from the group consisting of CN, $NO_2$ and $NH_2$.

36. A composition according to claim 35 wherein $R_1^1$ is acetoxymethyl, pivaloyloxymethyl, α-ethoxycarbonyloxyethyl or phthalidyl.

37. A composition according to claim 35 wherein the compound is of the formula (VI):

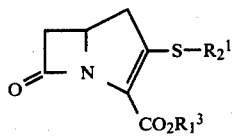

(VI)

wherein $R_1^3$ is tert-butyl, methyl, benzyl, p-nitrobenzyl, phthalidyl, pivaloyloxymethyl or sodium; and $R_2^1$ is p-acetamidophenyl, p-nitrophenyl, p-aminophenyl or p-(4'-nitrobenzyloxycarbonylamino)phenyl.

38. A composition according to claim 35 wherein $R_1^3$ is p-nitrobenzyl, phthalidyl or sodium.

39. A pharmaceutical composition according to claim 1 in oral administration form.

40. A pharmaceutical composition according to claim 1 in topical application form.

41. A pharmaceutical composition according to claim 1 in parenteral administration form.

42. A method for the treatment or prophylaxis of bacterial infections in humans and animals which comprises administering to a human or animal in need thereof an effective amount of the compound of the formula (II):

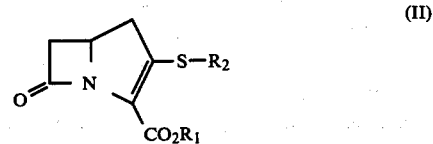

(II)

wherein $R_1$ is a group such that $CO_2R_1$ is a carboxylic acid group or a pharmaceutically acceptable salt or a lower alkyl ester, a lower alkoxyl lower alkyl ester, the benzyl ester, a lower alkoxy benzyl ester, a nitrobenzyl ester, a chlorobenzyl ester or an in-vivo hydrolyzable ester there or selected from the group consisting of the acetoxymethyl, pivaloyloxymethyl, α-ethoxycarbonyloxyethyl and phthalidyl esters and $R_2$ is phenyl or phenyl substituted by one to four substituents selected from the group consisting of lower alkyl, fluorine, chlorine, bromine, CH, $NO_2$, $COR_3$, $OR_3$, $SR_3$, $NH_2$, $NHCOR_3$, $NHCO_2R_3$, $CO_2R_3$ and $CO_2R_{10}$ wherein $R_3$ is lower alkyl, benzyl, fluorobenzyl, chlorobenzyl, bromobenzyl or nitrobenzyl and $CO_2R_{10}$ is carboxyl or a pharmaceutically acceptable salt thereof, not more than three such substituents being selected from the group consisting of fluorine, chlorine, bromine, CN, $NO_2$, $NH_2$, $COR_3$ and $CO_2R_3$ and not more than two such substituents being selected from from the group consisting of CN, $NO_2$ and $NH_2$.

43. A method according to claim 42 wherein $R_2$ is phenyl group or phenyl substituted by one or two substituents selected from the group consisting of fluorine, chlorine, bromine, CN, $NO_2$, $COR_3$, $OR_3$, $NHCOR_3$, $NHCO_2R_3$ and $CO_2R_3$ wherein $R_3$ is lower alkyl or benzyl.

44. A method according to claim 42 wherein $R_1$ is a group such that $CO_2R_1$ is a lower alkyl ester, a lower alkoxyl lower alkyl ester, the benzyl ester, a lower alkoxyl benzyl ester, a nitrobenzyl ester, a chlorobenzyl ester or an in-vivo hydrolyzable ester.

45. A method according to claim 42 wherein $R_2$ is phenyl, p-nitrophenyl, p-aminophenyl, p-acetamidophenyl or p-(4'-nitrobenzyloxycarbonylamino)phenyl.

46. A method according to claim 42 wherein $R_1$ is phthalidyl.

47. A method according to claim 42 wherein $R_1$ is p-nitrobenzyl.

48. A method according to claim 42 wherein $R_1$ is a group such that the compound is a carboxylic acid salt.

49. A method according to claim 42 wherein $R_1$ is sodium or potassium.

50. A method according to claim 42 wherein the compound is t-butyl 7-oxo-3-p-nitrophenylthio-1-azabicyclo[3.2.0-]hept-2-ene-2-carboxylic, t-butyl 7-oxo-3-phenylthio-1-azabicyclo[3.2.0]hept-2-ene-2-carboxylate, methyl 7-oxo-3-phenylthio-1-azabicyclo[3.2.0]hept-2-ene-2-carboxylate, benzyl 7-oxo-3-phenylthio-1-azabicyclo[3.2.0]hept-2-ene-2-carboxylate, p-nitrobenzyl 7-oxo-3-phenylthio-1-azabicyclo[3.2.0-]hept-2-ene-2-carboxylate, benzyl 7-oxo-3-p-acetamidophenylthio-1-azabicyclo[3.2.0]hept-2-ene-2-carboxylate, benzyl 7-oxo-3-p-aminophenylthio-1-azabicyclo[3.2.0]hept-2-ene-2-carboxylate, benzyl 7-oxo-3-p-(4'-nitrobenzyloxycarbonylamino)-phenylthio-1-azabicyclo[3.2.0]hept-2-ene-2-carboxylate, benzyl 7-oxo-3-p-nitrophenylthio-1-azabicyclo[3.2.0-]hept-2-ene-2-carboxylate, sodium 7-oxo-3-phenylthio-1-azabicyclo[3.2.0]hept-2-ene-2-carboxylate, phthalidyl 7-oxo-3-phenylthio-1-azabicyclo[3.2.0-]hept-2-ene-2-carboxylate or pivaloyloxymethyl 7-oxo-3-phenyl-1-azabicyclo[3.2.0]hept-2-ene-2-carboxylate.

51. A method according to claim 45 wherein R₁ is phthalidyl.

52. A method according to claim 45 wherein R₁ is p-nitrobenzyl.

53. A method according to claim 42 wherein R₂ is phenyl, p-chlorophenyl, m-chlorophenyl, p-nitrophenyl, m-nitrophenyl, p-ethoxycarbonylphenyl, p-fluorophenyl, p-methylphenyl, p-aminophenyl, p-acetamidophenyl, p-(4'-nitrobenzyloxycarbonylamino)phenyl or p-methoxyphenyl.

54. A method according to claim 42 wherein the compound has the R- configuration at C-5.

55. A method according to claim 42 wherein the compound has the S- configuration at C-5.

56. A method according to claim 42 wherein the compound is a mixture of isomers having the R- and S- configurations at C-5.

57. A method according to claim 42 wherein the compound is of the formula (IV):

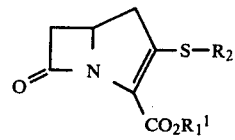

wherein $R_1^1$ is a group such that $CO_2R_1^1$ is an in-vivo hydrolyzable ester and $R_2$ is phenyl or phenyl substituted by one to four substituents selected from the group consisting of lower alkyl, fluorine, chlorine, bromine, CN, $NO_2$, $COR_3$, $OR_3$, $SR_3$, $NH_2$, $NHCOR_3$, $NHCO_2R_3$, $CO_2R_3$ and $CO_2R_{10}$ wherein $R_3$ is lower alkyl, benzyl, fluorobenzyl, chlorobenzyl, bromobenzyl or nitrobenzyl and $CO_2R_{10}$ is carboxyl or a pharmaceutically acceptable salt thereof, not more than three such substituents being selected from the group consisting of fluorine, chlorine, bromine, CN, $NO_2$, $NH_2$, $COR_3$ and $CO_2R_3$ and not more than two such substituents being selected from the group consisting of CN, $NO_2$ and $NH_2$.

58. A method according to claim 42 wherein $R_1^1$ is acetoxymethyl, pivaloyloxymethyl, α-ethoxycarbonyloxyethyl or phthalidyl.

59. A method according to claim 42 wherein the compound is of the formula (VI):

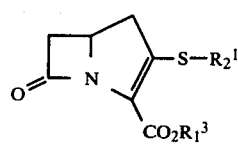

wherein $R_1^3$ is tert-butyl, methyl, benzyl, p-nitrobenzyl, phthalidyl, pivaloyloxymethyl or sodium; and $R_2^1$ is p-acetamidophenyl, p-nitrophenyl, p-aminophenyl or p-(4'-nitrobenzyloxycarbonylamino)phenyl.

60. A method according to claim 42 wherein $R_1^3$ is p-nitrobenzyl, phthalidyl or sodium.

61. A method according to claim 42 wherein the administration is oral.

62. A method according to claim 42 wherein the administration is by topical application.

63. A method according to claim 42 wherein the administration is parenteral.

64. A compound according to claim 7 wherein $R_2$ is phenyl.

65. A composition according to claim 76 wherein $R_2$ is phenyl.

66. A method according to claim 47 wherein $R_2$ is phenyl.

* * * * *